US010206880B2

(12) United States Patent
Adamer et al.

(10) Patent No.: US 10,206,880 B2
(45) Date of Patent: Feb. 19, 2019

(54) SOLID DISPERSION COMPRISING AN OREXIN RECEPTOR ANTAGONIST

(71) Applicant: Sandoz AG, Basel (CH)

(72) Inventors: Verena Adamer, Kundl (AT); Andreas Krekeler, Holzkirchen (DE); Michael Sedlmayr, Holzkirchen (DE)

(73) Assignee: Sandoz AG (CH)

( * ) Notice: Subject to any disclaimer, the term of this patent is extended or adjusted under 35 U.S.C. 154(b) by 31 days.

(21) Appl. No.: 15/303,336

(22) PCT Filed: Apr. 17, 2015

(86) PCT No.: PCT/EP2015/058426
§ 371 (c)(1),
(2) Date: Oct. 11, 2016

(87) PCT Pub. No.: WO2015/158910
PCT Pub. Date: Oct. 22, 2015

(65) Prior Publication Data
US 2017/0027873 A1 Feb. 2, 2017

(30) Foreign Application Priority Data
Apr. 17, 2014 (EP) .................................... 14165198

(51) Int. Cl.
*A61K 31/551* (2006.01)
*C07D 413/14* (2006.01)
*A61K 9/20* (2006.01)

(52) U.S. Cl.
CPC .......... *A61K 9/2022* (2013.01); *A61K 9/2009* (2013.01); *A61K 31/551* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 2003/0108616 A1 | 6/2003 | Bosch et al. | |
| 2008/0132490 A1 | 6/2008 | Bergman et al. | |

FOREIGN PATENT DOCUMENTS

| | | |
|---|---|---|
| CA | 2795550 A1 | 11/2013 |
| WO | 2008069997 A1 | 6/2008 |
| WO | 2010133611 A1 | 11/2010 |
| WO | 2011002285 A1 | 1/2011 |
| WO | 2012148553 A1 | 11/2012 |
| WO | 2013181174 A2 | 12/2013 |
| WO | 2014072961 A2 | 5/2014 |

OTHER PUBLICATIONS

PCT International Search Report and Written Opinion for PCT/EP2015/058426, dated Oct. 28, 2015, 18 pages.

*Primary Examiner* — Samantha L Shterengarts
(74) *Attorney, Agent, or Firm* — Luedeka Neely Group, P.C.

(57) ABSTRACT

A solid dispersion comprising suvorexant or a salt thereof in amorphous form and at least one pharmaceutically acceptable matrix compound, wherein the matrix compound is (i) a polymer and wherein the solid dispersion contains the suvorexant or salt thereof in an 5 amount of at least 50 weight-% based on the combined weight of the suvorexant or salt thereof and the at least one matrix compound, or (ii) a silicon-based inorganic adsorbent.

17 Claims, 25 Drawing Sheets

SOLID DISPERSION COMPRISING AN OREXIN RECEPTOR ANTAGONIST

This application is a Section 371 national phase entry of PCT application PCT/EP2015/058426, filed Apr. 17, 2015. This application also claims the benefit of the earlier filing date of European patent application 14165198.4, filed Apr. 17, 2014.

The present invention relates to a solid dispersion comprising suvorexant ([(7R)-4-(5-chloro-1,3-benzoxazol-2-yl)-7-methyl-1,4-diazepan-1-yl][5-methyl-2-(2H-1,2,3-triazol-2-yl)-phenyl] methanone) or a salt thereof in amorphous form as orexin receptor antagonist and at least one pharmaceutically acceptable matrix compound. Further, the present invention also relates to a process for preparing a solid dispersion comprising suvorexant or a salt thereof in amorphous form and at least one pharmaceutically acceptable matrix compound, as well as to a solid dispersion obtained or obtainable by said process. Further, the present invention relates to a pharmaceutical composition comprising such solid dispersion as well as a pharmaceutical composition for use in treating or preventing of a sleep disorder, wherein the pharmaceutical composition comprises such solid dispersion. Further, the present invention relates to a method for enhancing the quality of sleep in a mammalian patient in need thereof, a method for treating insomnia in a mammalian patient in need thereof as well as to a method for treating or controlling obesity in a mammalian patient in need thereof, these methods comprising administering the pharmaceutical composition comprising the solid dispersion to the mammalian patient.

BACKGROUND OF THE INVENTION

Orexin is a neurotransmitter that regulates wakefulness and appetite. Orexins are excitatory neuropeptides that have a critical role in maintaining wakefulness. Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hypeiprolactinemia; hypophysis tumour/adenoma; hypothalamic diseases; inflammatory bowel disease; gastric dyskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general and other diseases related to general orexin system dysfunction.

Some orexin receptor antagonists are capable of influencing at least some of the above described pathological conditions, in particular they are capable of promoting sleep in animals and humans are described in the art. One example for such an orexin receptor antagonist is [(7R)-4-(5-chloro-1,3-benzoxazol-2-yl)-7-methyl-1,4-diazepan-1-yl][5-methyl-2-(2H-1,2,3-triazol-2-yl)phenyl]methanone which has the structure according to Formula I

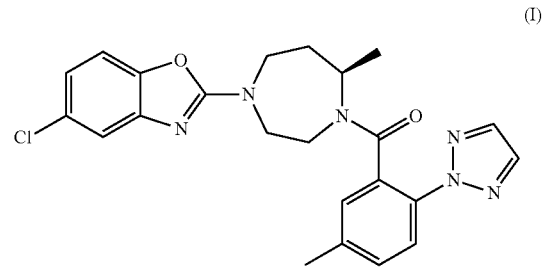 [SMILES: Cc1ccc(-n2nccn2)c(C(=O)N2CCN(c3nc4cc(Cl)ccc4o3)CC[C@H]2C)c1]

(I)

and which is e.g. described in US 20080132490 A1, WO 2008/069997 and Cox et al (2010) *Journal of Medicinal Chemistry*, 53 (14): 5320-5332. Alternative names for this compound are 5-chloro-2-{(5R)-5-methyl-4-[5-methyl-2-(2H-1,2,3-thiazol-2-yl)benzoyl]-1,4-diazepan-1-yl}-1,3-benzobenzoxazol and [(R)-4-(5-chloro-benzooxazol-2-yl)-7-methyl-[1,4]diazepan-1-yl]-(5-methyl-2-[1,2,3]triazol-2-yl-phenyl)-methanone.

The synthesis of [(7R)-4-(5-chloro-1,3-benzoxazol-2-yl)-7-methyl-1,4-diazepan-1-yl][5-methyl-2-(2H-1,2,3-triazol-2-yl)phenyl]methanone (hereinunder and above referred to as "Suvorexant" or "orexin receptor antagonist") is described in WO 2008/069997. According to WO 2008/069997 (Example 3) the compound is finally obtained as a white solid. As may be taken from the examples presented hereinunder, this solid is either the crystalline form I or the crystalline form II depending on the crystallization temperature employed. No amorphous form of suvorexant is described in WO 2008/069997.

The crystalline forms I and II of [(7R)-4-(5-chloro-1,3-benzoxazol-2-yl)-7-methyl-1,4-diazepan-1-yl][5-methyl-2-(2H-1,2,3-triazol-2-yl)phenyl]methanone are further explicitly described in WO 2012/148553 A1. There it is stated that forms I and II are enantiotropically related with a transition temperature of 35-40° C. Moreover, a pharmaceutical composition comprising a crystalline form of [(7R)-4-(5-chloro-1,3-benzoxazol-2-yl)-7-methyl-1,4-diazepan-1-yl][5-methyl-2-(2H-1,2,3-triazol-2-yl)phenyl]methanone is described. However, the crystalline forms of suvorexant only show limited solubility and bioavailability.

Thus, WO 2013/181174 proposes compositions comprising suvorexant together with a concentration enhancing polymer, which form together an amorphous dispersion. The composition however only comprises about 4% to 40% suvorexant.

Thus, there is still there is still the need for advantageous compositions comprising a high amount of suvorexant which show a high solubility and/or bioavailability and a long-term stability.

Therefore, it was an object of the present invention to provide compositions comprising suvorexant, which compositions have advantageous characteristics regarding solubility and/or bioavailability and/or the stability.

SUMMARY OF THE INVENTION

Surprisingly, it was found that this object can be solved by providing a solid dispersion comprising, preferably consisting of, suvorexant or a salt thereof in amorphous form and at least one pharmaceutically acceptable matrix compound and wherein the at least one matrix compound is
(i) a polymer and wherein the solid dispersion contains the suvorexant or salt thereof in an amount of at least 50 weight-% based on the combined weight of the suvorexant or salt thereof and the at least one matrix compound, or
(ii) a silicon-based inorganic adsorbent.

Further, the present invention provides for preparing a solid dispersion comprising suvorexant or a salt thereof in amorphous form and at least one pharmaceutically acceptable matrix compound, the process comprising
(a) providing suvorexant or a salt thereof
(b) dissolving or dispersing suvorexant provided in (a) and the at least one matrix compound in a solvent to form a mixture
(c) removing at least part, preferably essentially all, of the solvent
to give the solid dispersion, wherein the at least one matrix compound is
(i) a polymer and wherein the solid dispersion contains the suvorexant or salt thereof in an amount of at least 50 weight-% based on the combined weight of the suvorexant or salt thereof and the at least one matrix compound, or
(ii) a silicon-based inorganic adsorbent.

Further, the present invention relates to a process for preparing a solid dispersion comprising suvorexant or a salt thereof in amorphous form, the process comprising
(a) providing suvorexant or a salt thereof
(b) dissolving or dispersing suvorexant provided in (a) in a solvent to form a mixture
(c) removing at least part, preferably essentially all, of the solvent by spray drying, to give the solid dispersion.

Further, the present invention relates to a process for preparing a solid dispersion comprising suvorexant or a salt thereof in amorphous form and at least one pharmaceutically acceptable matrix compound, the process comprising
(a') providing suvorexant or a salt thereof
(b') mixing the suvorexant provided in (a') and the at least one matrix compound to form a mixture
(c') milling the mixture according to (b')
to give the solid dispersion, and wherein the matrix compound is
(i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
(ii) a silicon-based inorganic adsorbent.

Further, the present invention relates to a process for preparing a solid dispersion comprising suvorexant or a salt thereof in amorphous form and at least one pharmaceutically acceptable matrix compound, the process comprising
(a') providing suvorexant or a salt thereof
(b') mixing the suvorexant provided in (a') and the at least one matrix compound to form a mixture
(c') milling the mixture according to (b')
to give the solid dispersion.

Further, the present invention relates to a solid dispersion obtained or obtainable by the above-described processes as well as to a pharmaceutical composition comprising a solid dispersion as described above, or a solid dispersion obtained or obtainable by the above-described processes.

DETAILED DESCRIPTION

In a first aspect, the present invention provides a solid dispersion comprising suvorexant ([(7R)-4-(5-chloro-1,3-benzoxazol-2-yl)-7-methyl-1,4-diazepan-1-yl] [5-methyl-2-(2H-1,2,3-triazol-2-yl)phenyl] methanone) or a salt thereof in amorphous form and at least one matrix compound, wherein the at least one matrix compound is
(i) a polymer and wherein the solid dispersion contains the suvorexant or salt thereof in an amount of at least 50 weight-% based on the combined weight of the suvorexant or salt thereof and the at least one matrix compound, or
(ii) a silicon-based inorganic adsorbent.

Further, the present invention relates to a process for preparing such solid dispersion.

Surprisingly it has been found that though the amorphous form of suvorexant as such turned out to be unstable, a stable solid dispersion comprising suvorexant in amorphous form may be provided when combining the suvorexant with at least one matrix compound. It is contemplated that this surprisingly stable amorphous form is advantageous with respect to its solubility as well as bioavailability when compared to the crystalline forms described in the prior art. Further, this solid dispersion shows advantageous long term stability.

Further, compared to the teaching of the prior art, the present invention provides the possibility to provide compositions having a high suvorexant content, such as in an amount of at least 50 weight-% based on the combined weight of the suvorexant or salt thereof and the at least one matrix compound, which allow to administer the suvorexant to a patient in need thereof with only a few or even only one dosage. Further in particular with regard to dosage forms such as tablets, these high suvorexant contents allow to prepare smaller tablets which can be swallowed easily by the patient.

Amorphous Suvorexant

As described above, the solid dispersion according to the present invention comprises suvorexant or a salt thereof in amorphous form, and at least one matrix compound.

"Amorphous" in the context of the invention means that the solid phase is in a non-crystalline state. Amorphous solids generally possess crystal-like short-range molecular arrangements, i.e. no long-range order of molecular packing is found in crystalline solids. The solid state form of a solid, such as of the orexin receptor antagonists in the solid dispersion may be determined by polarized light microscopy, X-ray powder diffraction, differential scanning calorimetry or other techniques known to those of skill in the art. The term "comprising" suvorexant or a salt thereof in amorphous form is denoted to mean that at least 80% by weight, more preferably at least 85% by weight, more preferably at least 90% by weight, more preferably at least 95% by weight, more preferably at least 96% by weight, more preferably at least 97%, more preferably at least 98% by weight, more preferably at least by weight 99% by weight, more preferably at least by weight 99.9% by weight, more preferably all of the suvorexant present in the solid dispersion is present in amorphous form.

Besides the amorphous form of suvorexant or a salt thereof, the solid dispersion may comprise crystalline forms of suvorexant. However, preferably, less than 20% by weight, more preferably less than 15% by weight, more preferably less than 10% by weight, more preferably less than 5% by weight, more preferably less than 4% by weight, more preferably less than 3%, more preferably less than 2% by weight, more preferably less than 1% by weight, more preferably less than 0.1% by weight, more preferably 0% by weight of all suvorexant present in the solid dispersion is present in crystalline form. Preferably the solid dispersion thus does not comprise any suvorexant in crystalline form.

Thus, the present invention preferably relates to a solid dispersion, as described above, wherein at least 80% by weight, more preferably at least 85% by weight, more preferably at least 90% by weight, more preferably at least 95% by weight, more preferably at least 96% by weight, more preferably at least 97%, more preferably at least 98% by weight, more preferably at least by weight 99% by weight, more preferably at least by weight 99.9% by weight, more preferably all of the suvorexant present in the solid dispersion is present in amorphous form. Likewise, the present invention relates to a process for preparing a solid dispersion, as described above, wherein at least 80% by weight, more preferably at least 85% by weight, more preferably at least 90% by weight, more preferably at least 95% by weight, more preferably at least 96% by weight, more preferably at least 97%, more preferably at least 98% by weight, more preferably at least by weight 99% by weight, more preferably at least by weight 99.9% by weight, more preferably all of the suvorexant present in the solid dispersion is present in amorphous form.

Solid Dispersion

The term "solid dispersion" refers to a composition in a solid state, i.e. a state which is neither liquid nor gaseous, wherein the suvorexant is dispersed in at least one of the at least one pharmaceutically acceptable matrix compounds comprised in the solid dispersion, preferably in all of the pharmaceutically acceptable matrix compounds comprised in the solid dispersion.

Preferably the solid dispersion consist of suvorexant and the at least one matrix compound. Preferably, the at least one matrix compound forms a matrix which may be either crystalline or amorphous or a mixture thereof. Suvorexant can in principle be dispersed in the matrix molecularly, in purely amorphous particles or in amorphous and crystalline particles, as described above.

The term "solid dispersion" as used herein encompasses all known categories of solid dispersions, i.e. simple eutectic mixtures, solid solutions, such as continuous solid solutions, discontinued solid solutions, substitutional crystalline, interstitial crystalline and amorphous solid solutions, glass solutions and amorphous precipitations in crystalline carriers. Preferably, the solid dispersion according to the present invention is an amorphous solid solution.

Preferably, the solid dispersion according to the invention is an amorphous solid dispersion. The term "amorphous solid dispersion" as used herein refers to solid dispersions comprising suvorexant in a substantially amorphous solid form. Preferably, amorphous particles of suvorexant are dispersed in the polymer matrix.

The term "substantially amorphous solid form" is denoted to mean that at least 80% by weight, more preferably at least 85% by weight, more preferably at least 90% by weight, more preferably at least 95% by weight, more preferably at least 96% by weight, more preferably at least 97%, more preferably at least 98% by weight, more preferably at least by weight 99% by weight, more preferably at least by weight 99.9% by weight, more preferably all of the orexin receptor antagonists, i.e. suvorexant or the salt thereof, are present in amorphous form.

Matrix Compound

Regarding the at least one pharmaceutically acceptable matrix compound, this at least one matrix compound is either a polymer or a silicon-based inorganic adsorbent, as mentioned above. It is to be understood that the solid dispersion may comprise more than one matrix compound, such as two, three, four, five, six, seven, eight, nine or ten matrix compounds. In case, more than one matrix compound is present, a mixture of at least one polymer and at least one silicon-based inorganic adsorbent may also be present. Preferably, the solid dispersion comprises one matrix compound.

It was surprisingly found that matrix compounds which exhibit specific characteristics when subjected to a dynamic vapor sorption measurement are especially suitable as matrix compounds according to the present invention. In particular, it was found that these matrix compounds can stabilize amorphous suvorexant in the solid dispersion according to the present invention even at high suvorexant contents, such as suvorexant contents in the range of from 50 to 95 weight-%. Thus, although at such high suvorexant contents, the respective amount of matrix compound contained in the solid dispersion is necessarily low, the matrix compounds exhibiting specific characteristics when subjected to a dynamic vapor sorption measurement can stabilize the suvorexant in its amorphous form. Hence, it was surprisingly found that although the suvorexant content of the preferred solid dispersions of the present invention is significantly higher than those taught in the art, thus having a significantly lower content of stabilizing matrix compounds, in particular the preferred matrix compounds described above allow to provide stable solid dispersions which, even at humidity of stress conditions (i.e. 75% relative humidity at 40° C.), do not show deliquescence. Still further, it was found that the amorphous suvorexant comprised in the preferred solid dispersions of the present invention does not show any tendency to crystallize in the solid dispersions according to the present invention.

Therefore, the present invention relates to the solid dispersions described above, having a moisture stability of at least 95%, preferably at least 98%, more preferably at least 99%, wherein the moisture stability is defined as the amount of solid amorphous suvorexant which is present in the solid dispersions (solid compositions) after having been exposed to a relative humidity of 75% at 40° C. for 4 weeks, relative to the amount of solid amorphous suvorexant which is present in the solid dispersion before said exposure. The term "before said exposure" as used in this context of the present application relates to a solid dispersion which, prior to being exposed to a relative humidity of 75% at 40° C., has been stored, directly after its preparation, at a relative humidity in the range of from 30% at a temperature of 25° C. Therefore, the present invention also relates to the solid dispersions described above, having a moisture stability of at least 95%, preferably at least 98%, more preferably at least 99%, wherein the moisture stability is defined as the amount of solid amorphous suvorexant which is present in the solid dispersion after having been exposed to a relative humidity of 75% at 40° C. for 4 weeks, relative to the amount of solid amorphous suvorexant which is present in the solid dispersion when, directly after its preparation, being stored at a relative humidity a relative humidity in the range of from 30% at a temperature of 25° C.

Regarding the specific characteristics of the preferred matrix compounds according to the present invention when subjected to a dynamic vapor sorption measurement, it was found that in the adsorption-desorption isotherm of the at least one matrix compounds, the mass difference Δm(adsorption) between 50% and 90% relative humidity at 25° C. is greater than or equal to 40%, preferably in the range of from 40 to 80%, more preferably in the range of from 45 to 78%, determined according to dynamic vapor sorption measurement.

Further, preferably, in the adsorption-desorption isotherm of the at least one matrix compounds, the mass difference Δm(adsorption) between 0 and less than 50% relative humidity at 25° C. is less than or equal to 20%, preferably less than 15%, more preferably less than 12%, more preferably less than 10%, determined according to dynamic vapor sorption measurement.

Without wanting to be bound by any theory, it is believed that the specific pore properties and/or the specific surface properties, either regarding the respective chemical and/or the physical nature thereof, of the preferred matrix compounds may lead to their specific and advantageous suitability for stabilizing the amorphous suvorexant in the solid dispersions, even at low matrix compound contents of the solid dispersions. Regarding the dynamic vapor sorption measurements and the determination of the values of Δm(desorption) and Δm(adsorption) at 75% relative humidity and 25° C., specific reference is made to example V of the present invention.

The Polymer

According to one preferred embodiment (embodiment (i)), the at least one matrix compound is at least one polymer. Preferably, the solid dispersion comprises only one matrix component which is a polymer.

According to this embodiment, the solid dispersion contains the suvorexant or salt thereof in an amount of at least 50 weight-%, preferably more than 50 weight-%, more preferably at least 51 weight-%, more preferably at least 55 weight-%, based on the combined weight of the suvorexant or salt thereof and the at least one matrix compound. Preferably, the solid dispersion contains the suvorexant or the at least one salt thereof in an amount of at least 60 weight-%, more preferably at least 70% by weight, more preferably at least 80% by weight, most preferably in the range of from 80% to 95% by weight, based on the combined weight of the suvorexant or the at least one salt thereof and the at least one matrix compound. Preferred ranges are from 51 to 95 weight-% or from 55 to 95 weight-% or from 60 to 95 weight-% or from 70 to 95 weight-% or from 80 to 95 weight-%.

Polymers which are suitable for use in the dispersion of the present invention are preferably polymers which are pharmaceutically acceptable, in particular for oral administrations, to a mammal such as a human. Preferably, the polymer is a polymer selected from the group consisting of celluloses, hydroxyalkylcellulose, polyethyleneglycols, polyvinylalcohols, vinylpyrrolidone/vinylacetate copolymers, polyvinyl caprolactam/polyvinyl acetate/polyethylene glycol copolymers and mixtures and copolymers thereof.

As suitable examples for celluloses, cellulose acetate phthalates, carboxymethyl celluloses and carboxymethyl celluloses and carboxyethyl celluloses are mentioned. It is to be understood that this includes derivatives of the above-mentioned polymers such as chemically modified derivatives thereof. In case the polymer is a hydroxyalkyl cellulose, the polymer is preferably a hydroxymethyl cellulose, a hydroxypropyl cellulose, a hydroxypropylmethyl cellulose or a hydroxymethyl cellulose acetate succinate. Suitable examples for celluloses as such are cellulose acetate phthalates, carboxymethyl cellulose and carboxyethyl cellulose. The term "cellulose acetate phthalate" refers to any of the family of cellulose polymers that have acetate and phthalate groups attached by ester linkage to a significant fraction of the cellulose polymer's hydroxyl groups.

Preferably, the polymer is selected from the group consisting of hydroxymethyl cellulose, hydroxypropyl cellulose, hydroxypropylmethyl cellulose, hydroxymethyl cellulose acetate succinate, hydroxypropylmethyl cellulose acetate succinate, hydroxypropylmethyl cellulose acetate phthalate, hydroxypropylmethyl cellulose acetate, hydroxypropylmethyl cellulose succinate, hydroxypropylmethyl cellulose phthalate, hydroxypropylmethyl cellulose, hydroxypropyl cellulose, methyl cellulose, hydroxyethyl cellulose, hydroxyethylmethyl cellulose, hydroxyethyl cellulose acetate, hydroxyethylethyl cellulose, hydroxyethylmethyl cellulose acetate succinate, hydroxyethyl methyl cellulose acetate phthalate, carboxymethyl cellulose, carboxyethyl cellulose, polyethyleneglycol, polyvinylalcohol, vinylpyrrolidone/vinylacetate copolymers, polyvinylcaprolactam polyvinylacetate polyethyleneglycol copolymers and mixtures or copolymers thereof. In case the polymer is a polyvinylcaprolactam polyvinylacetate polyethyleneglycol copolymer, the polymer is preferably a graft polymer. The term "graft polymer" as used herein refers to a branched copolymer in which the side chains are structurally distinct from the main chain. Preferably, these graft polymers are based on polyethers and are obtained via free radical polymerization of the vinyl monomers in the presence of polyethers. In case of a polyvinylcaprolactam polyvinylacetate polyethyleneglycol graft polymer, a vinylcaprolactam and vinylacetate are used as vinyl monomers. Graft polymers of this type are commercially available as Soluplus®, BASF.

More preferably, the polymer is selected from the group consisting of hydroxymethyl cellulose, hydroxypropyl cellulose, polyethylene glycol, polyvinyl alcohol, hydroxypropylmethyl cellulose, hydroxymethyl cellulose acetate succinate, vinylpyrrolidone/vinylacetate copolymers and polyvinylcaprolactam polyvinylacetate polyethylene glycol graft polymers.

Thus, the present invention also relates to a solid dispersion, as described above, wherein the polymer is selected from the group consisting of hydroxymethyl cellulose, polyvinylpyrrolidone, hydroxypropyl cellulose, polyethylene glycol, polyvinyl alcohol, hydroxypropylmethyl cellulose, hydroxymethyl cellulose acetate succinate, vinylpyrrolidone/vinylacetate copolymers and polyvinylcaprolactam polyvinylacetate polyethylene glycol graft polymers, wherein preferably at least 80% by weight of all suvorexant present in the solid dispersion is present in amorphous form. Likewise, the present invention relates to a process for preparing a solid dispersion and a solid dispersion obtained or obtainable by said process, wherein step (b) comprises dissolving suvorexant and a polymer in a solvent to form a solution, wherein the polymer is selected from the group consisting of hydroxymethyl cellulose, polyvinylpyrrolidone, hydroxypropyl cellulose, polyethylene glycol, polyvinyl alcohol, hydroxypropylmethyl cellulose, hydroxymethyl cellulose acetate succinate, vinylpyrrolidone/vinylacetate copolymers and polyvinylcaprolactam polyvinylacetate polyethylene glycol graft polymers.

Most preferably, the polymer is a hydroxyalkylalkylcellulose or a polyvinylcaprolactam-polyvinylacetate-polyethylene glycol graft polymer, more preferably a polyvinylcaprolactam-polyvinylacetate-polyethylene glycol graft polymer.

Preferably, the weight average molecular weight ($M_w$) of the hydroxyalkylalkylcellulose, more preferably the hydroxypropylmethylcellulose, is in the range of from 7 to 225 kDa, more preferably in the range of from 7 to 100 kDa, more preferably in the range of from 7 to 30 kDa. According to the present invention, it is possible that the solid dispersion contains two or more cellulose derivative, preferably two or more hydroxyalkylalkylcelluloses, more preferably two or more hydroxypropylmethylcelluloses which differ only in the weight average molecular weight $M_w$.

Preferably, the molecular degree of substitution (DS) of the hydroxyalkylalkylcellulose, more preferably the hydroxypropylmethylcellulose, is in the range of from 0.3 to 2.8, preferably in the range of from 0.6 to 2.5, more preferably in the range of from 1.0 to 2.3, more preferably in the range of from 1.3 to 2.0. According to the present invention, it is possible that the solid dispersion contains two or more cellulose derivative, preferably two or more hydroxyalkylalkylcelluloses, more preferably two or more hydroxypropylmethylcelluloses which differ only in the molecular degree of substitution. The parameter DS describes the number of hydroxyalkylalkylated sites per anhydroglucose unit of a given hydroxyalkylalkylcellulose.

Preferably, the at least one hydrophilic, preferably water-soluble, polymer has a solubility in water of at least 10 g/l, more preferably of at least 15 g/l, more preferably of at least 20 g/l, more preferably of at least 25 g/l, more preferably of at least 30 g/l, in each case at 23° C. at atmospheric pressure.

Surprisingly, it has been found that, when using a polymer as described above, suvorexant may be stabilized in amorphous form. In other words, a stable solid dispersion comprising suvorexant in amorphous form is provided. The term "stable" in this context is denoted to mean that the total amount of suvorexant present in amorphous form present in the solid dispersion does not change over a time up to 4 weeks, in particular when exposed to 75% relative humidity at 40° C. for four weeks.

The at least one polymer forms a matrix which may be either crystalline or amorphous or a mixture thereof. Preferably, the polymer forms a matrix which is amorphous. The term "amorphous" in this context is denoted to mean that at least 80% by weight, more preferably at least 85% by weight, more preferably at least 90% by weight, more preferably at least 95% by weight, more preferably at least 96% by weight, more preferably at least 97% by weight, more preferably at least 98% by weight, more preferably at least 99% by weight, more preferably at least 99.9% by weight, more preferably all of the polymer(s) present in the solid dispersion is/are present in amorphous form.

The Silicon-Based Inorganic Adsorbent

According to one preferred embodiment (embodiment (ii)), the at least one matrix compound is at least one silicon-based inorganic adsorbent. Preferably, the solid dispersion comprises only one matrix component which is a silicon-based inorganic adsorbents.

Preferably, the solid dispersion in (ii) contains the suvorexant or the at least one salt thereof in an amount in the range of from 10 to 70 weight-%, more preferably in the range of from 20 to 65% by weight, more preferably in the range of from 30 to 60% by weight, more preferably in the range of from 35 to 55% by weight, more preferably in the range of from 40 to 55% by weight, more preferably in the range of from 45 to 55% by weight, based on the combined weight of the suvorexant or the at least one salt thereof and the at least one matrix compound.

Examples of silicon-based inorganic adsorbents include, but are not restricted to, silica, silicates, and a combination of two or more thereof. For example, the silicon-based inorganic adsorbent is selected from the group consisting of silicas and combinations of two or more thereof; or from the group consisting of silicates and combinations of two or more thereof; or from the group consisting of at least one silicate. The term "silicate" as used in this context of the present invention refers to naturally occurring or synthesized compounds containing an anionic silicon compound, preferably an oxide. Examples of such silicates include, but are not restricted to, nesosilicates comprising the structure unit $[SiO_4]^{4-}$, sorosilicates comprising the structure unit $[Si_2O_7]^{6-}$, cyclosilicates comprising the structure unit $[Si_nO_{3n}]^{2n-}$, single chain inosilicates comprising the structure unit $[Si_nO_{3n}]^{2n-}$, double chain inosilicates comprising the structure unit $[Si_{4n}O_{11n}]^{6n-}$, phyllosilicates comprising the structure unit $[Si_nO_{5n}]^{2n-}$, or tectosilicates with a 3D framework comprising the structure unit $[Al_xSi_yO_{2(x+y)}]^{x-}$. The term "silica" as used in this context of the present invention refers to naturally occurring or synthesized silica. Examples of such silica include, but are not restricted to fumed silica, precipitated silica, gel silica, colloidal silica.

Surprisingly, it was found that silicon-based inorganic adsorbents are preferred, wherein in the adsorption-desorption isotherm of the at least one matrix compound in (ii), the mass difference Δm(adsorption) between 50 and 90% relative humidity at 25° C. is greater than or equal to 40%, preferably greater than or equal to 42%, more greater than or equal to 44%, more preferably greater than or equal to 45%, determined according to dynamic vapor sorption measurement.

Preferably, the adsorption-desorption isotherm of the at least one matrix compound in (ii), the mass difference Δm(adsorption) between 0 and less than 50% relative humidity at 25° C. is less than or equal to 20%, preferably less than or equal to 15%, more preferably less than or equal to 12%, more preferably less than or equal to 10%, determined according to dynamic vapor sorption measurement.

Preferably, in the adsorption-desorption isotherm of the at least one matrix compound in (ii), the mass difference Δm(desorption) at 75% relative humidity and 25° C. is greater than or equal to the mass difference Δm(adsorption) at 75% relative humidity and 25° C., determined according to dynamic vapor sorption measurement.

Preferably the silicon-based inorganic adsorbent has a pH of at least 6.0. More preferably, the silicon-based inorganic adsorbent has a pH in the range of from 6.0 to 9.0, more preferably in the range of from 6.5 to 8.5, more preferably in the range of from 6.8 to 8.0. The pH is to be understood as being determined by suspending 2 g of the respective adsorbent in 50 ml water, stirring the suspension, allowing the stirred suspension to stand for two minutes and determining the pH with a pH meter at room temperature.

Generally, it is conceivable that the solid dispersion of the present invention contains at least one silicon-based inorganic adsorbent having a pH in the above-defined preferred ranges and at least one silicon-based inorganic adsorbent having a pH outside these ranges. Preferably, all silicon-based inorganic adsorbents comprised in the solid dispersion of the present invention have a pH in the above-defined preferred ranges.

Preferably, the oil adsorbance of the at least one silicon-based inorganic adsorbent is in the range of from 1.0 to 5.0 ml/g, preferably in the range of from 1.3 to 4.5 ml/g, more preferably in the range of from 1.5 to 4.0 ml/g, more preferably in the range of from 2 to 3.5 ml/g. Generally, it is conceivable that the solid dispersion of the present invention contains at least one silicon-based inorganic adsorbent having an oil adsorbance in the above-defined preferred ranges and at least one silicon-based inorganic adsorbent having an oil adsorbance outside these ranges. Preferably, all silicon-based inorganic adsorbents comprised in the solid dispersion of the present invention have an oil adsorbance in the above-defined preferred ranges.

Preferably, the bulk density of the at least one silicon-based inorganic adsorbent is in the range of from 0.05 to 0.25 g/ml, preferably in the range of from 0.10 to 0.16 g/ml, more preferably in the range of from 0.10 to 0.16 g/ml Generally, it is conceivable that the solid dispersion of the present invention contains at least one silicon-based inorganic adsorbent having a bulk density in the above-defined preferred ranges and at least one silicon-based inorganic adsorbent having a bulk density outside these ranges. Preferably, all silicon-based inorganic adsorbents comprised in the solid dispersion of the present invention have having a bulk density in the above-defined preferred ranges.

Preferably, the silica is selected from the group consisting of fumed silica, precipitated silica, gel silica, colloidal silica, and a combination of two or more thereof, such as a combination of fumed silica and precipitated silica or a combination of fumed silica and colloidal silica or a combination of fumed silica and gel silica or a combination of precipitated silica and gel silica or a combination of precipitated silica and colloidal silica or a combination of gel silica and colloidal silica or a combination of fumed silica and precipitated silica and gel silica or a combination or fumed silica and gel silica and colloidal silica or a combination of precipitated silica and gel silica and colloidal silica or a combination of fumed silica and precipitated silica and gel silica and colloidal silica. Preferred silica include, but are not restricted to, the commercially available compounds Syloid® 72 FP, Syloid® 244 FP, both from Grace.

Preferably, the silicate is an aluminosilicate which, more preferably, additionally contains at least one alkali metal element selected from the group consisting of Li, Na, K, Rb, Cs and a combination of two or more thereof, preferably from the group consisting of Li, Na, K, and a combination of two or more thereof, more preferably from the group consisting of Na, K, and a combination of two or more thereof, and/or at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminosilicate which additionally contains at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminosilicate which additionally contains Mg. Preferred silicates include, but are not restricted to, the commercially available compounds Neusilin® UFL2, Neusilin® US2, both from Fuji Chemical Industry Co., Ltd.

Therefore, the present invention also relates to the solid dispersion as described above, wherein the at least one silicon-based inorganic adsorbent is selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium.

Thus, the present invention also relates to solid dispersion, as described above, and to a process for preparing a solid dispersion, as described above, wherein the at least one matrix compound is at least one silicon-based inorganic adsorbent, and wherein the at least one silicon-based inorganic adsorbent is selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium, wherein more preferably, at least 90 weight-%, more preferably at least 95 weight-%, more preferably at least 99 weight-% of the at least one silicon-based inorganic adsorbent are present in amorphous form.

Generally, the silica and/or the silicate can be present in crystalline or amorphous form. Preferably, at least 90 weight-%, more preferably at least 95 weight-%, more preferably at least 99 weight-% of the at least one silicon-based inorganic adsorbent are present in amorphous form. More preferably, at least 99.5 weight-%, more preferably at least 99.9 weight-%, more preferably at least 99.99 weight-% of the at least one silicon-based inorganic adsorbent are present in amorphous form.

According to this embodiment, the solid dispersion contains the suvorexant or salt thereof preferably silicon-based inorganic adsorbent, based on the combined weight of the suvorexant or the at least one salt thereof and the at least one matrix compound (sum of all matrix compounds).

Pharmaceutically Acceptable Salts

As described above, the compounds of the present invention can be present as pharmaceutically acceptable salts. The term "pharmaceutically acceptable salts" refers to salts prepared from pharmaceutically acceptable, preferably non-toxic, bases or acids including mineral or organic acids or organic or inorganic bases. Such salts are also known as acid addition and base addition salts. Acids commonly employed from acid addition salts are inorganic acids such as hydrochloric acid, hydrobromic acid, hydroiodic acid, sulfuric acid, phosphoric acid and the like, and organic acids such as para-toluene sulfonic acid, methane sulfonic acid, oxalic acid, para-bromophenylsulfonic acid, carbonic acid, succinic acid, citric acid, benzoic acid, acidic acid and the like. Examples of pharmaceutically acceptable salts are sulfates, pyrosulfates, bisulfates, sulfites, bisulfites, phosphates, monohydrogenphosphates, dihydrogenphosphates, metaphosphates, pyrophosphates, bromides, iodides, acetates, propionates, dicanoates, caprolates, acrylates, formates hydrochlorides, dihydrochlorides, isobutyrates, caproates, heptanoates, propiolates, oxalates, malonates, succinates, suberates, sebacates, fumarates, maleates, butin-1,4-dioates, hexin-1,6-dioates, benzoates, chlorobenzoates, methylbenzoates, hydroxybenzoates, methoxybenzoates, phthalates, xylenesulfates, phenylacetates, phenyl propionates, phenyl butyrates, citrates, lactates, gamma-hydroxybutyrrates, glycolates, tartrates, methanesulfonates, propanesulfonates, naphthalene-1-sulfonates, naphthalene-2-sulfonates, mandelates and salts derived from other primary, secondary or tertiary amines including amines such as arginines, betaines, caffeines, cholines, N,N'-dibenzylethylenediamines, diethyleneethylamines, 2-diethylaminoethanols, 2-dimethylaminoethanols, ethanolamines, ethylenediamines, N-ethylmorpholines, N-ethylpiperidines, cocamines, glucosamines, histidines, hydrabamines, isopropylamines, lysines, methylglucamines, morpholines, piperazines, piperidines, polyamine resins, purines, thiobromines, triethylamines, trimethylamines, tripropylamines, tromethamines and the like. Preferred pharmaceutically acceptable acid addition salts are those formed with mineral acids such as hydrochloric acid and hydrobromic acid and those formed with organic acids such as malic acid and methanesulfonic acid. Further salts derived from inorganic bases including aluminum, ammonium, calcium, copper, ferric, ferrous, lithium, magnesium, manganic, manganous, potassium, sodium, zinc salts and the like should be mentioned.

Besides the above-mentioned components, i.e. suvorexant and the polymer, the solid dispersion may comprise further components such as further orexin antagonists, further polymers, optionally at least one solvent, and the like.

Preferably, the solid dispersion comprises no further orexin antagonists besides suvorexant.

As describe above, the solid dispersion may comprise at least one solvent, such as the solvent used in the process for preparing the solid dispersion. In case the solid dispersion comprises at least one solvent, the amount of solvent present in the solid dispersion is preferably less than 5% by weight, more preferably less than 4% by weight, more preferably less than 3% by weight, more preferably less than 2% by weight, more preferably less than 1% by weight, more preferably less than 0.5% by weight, based on the total weight of the solid dispersion.

Preferably, the solid dispersion according to the invention consists of suvorexant or a salt thereof and the polymer and optionally the at least one solvent, wherein the solvent is preferably present in an amount of less than 5% by weight, more preferably less than 4% by weight, more preferably less than 3% by weight, more preferably less than 2% by weight, more preferably less than 1% by weight, more preferably less than 0.5% by weight, based on the total weight of the solid dispersion. More preferably, the solid dispersion as described above consists of the suvorexant or salt thereof and the polymer.

Also preferably, the solid dispersion comprises a nonionic surfactant, preferably a block copolymer of ethylene oxide and propylene oxide, more preferably a block copolymer of ethylene oxide and propylene oxide according to the following formula:

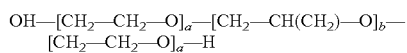

With regard to the indices a and b, no specific restrictions exist. Preferably, a is in the range of from 50 to 150, preferably from 60 to 130, more preferably from 70 to 110. Preferably, b is in the range of from 10 to 80, preferably of from 20 to 70, more preferably of from 30 to 60. Preferred block copolymer of ethylene oxide and propylene oxide may be obtained commercially, for example as Kolliphor® P 188, Kolliphor® P 237, Kolliphor® P 338 or Kolliphor® P 407. Regarding a preferred block copolymer of ethylene oxide and propylene oxide, a is in the range of from 75 to 85 and b is in the range of from 25 to 30. Such a preferred block copolymer may be obtained commercially, for example Kolliphor® P 188.

The solid dispersion may contain the nonionic surfactant in an amount in the range of from 0.1 to 10 weight-% or from 0.5 to 9 weight-% or from 1 to 8 weight-% or from 2 to 7 weight-% or from 3 to 6 weight-%, based on the total weight of the solid dispersion.

Preferably, the solid dispersion according to the invention consists of suvorexant or a salt thereof, the polymer, the nonionic surfactant and optionally the at least one solvent, wherein the solvent is preferably present in an amount of less than 5% by weight, more preferably less than 4% by weight, more preferably less than 3% by weight, more preferably less than 2% by weight, more preferably less than 1% by weight, more preferably less than 0.5% by weight, based on the total weight of the solid dispersion. More preferably, the solid dispersion as described above consists of the suvorexant or salt thereof, the polymer and the nonionic surfactant.

Process for Preparing the Solid Dispersion

As described above, the present invention also relates to a process for preparing a solid dispersion comprising suvorexant or salt thereof in amorphous form and at least one pharmaceutically acceptable matrix compound, the process comprising (a) providing suvorexant or a salt thereof
(b) dissolving or dispersing suvorexant provided in (a) and the at least one matrix compound in a solvent to form a mixture, optionally in the presence of a surfactant, preferably a nonionic surfactant
(c) removing at least part, preferably essentially all, of the solvent to give the solid dispersion, and wherein the at least one matrix compound is (i) a polymer and wherein the solid dispersion contains the suvorexant or salt thereof in an amount of at least 50 weight-% based on the combined weight of the suvorexant or salt thereof and the at least one matrix compound, or
(ii) a silicon-based inorganic adsorbent.

Step (a)

The provision of suvorexant may be carried out by any method known to the person skilled in the art, such as, e.g., the methods described in WO 2012/148553 A1. Suvorexant may be provided in any form, such as in crystalline or in amorphous form or as a mixture of crystalline and amorphous form. Preferably, the compound in step (a) is provided in crystalline form such as described in WO 2012/148553 A1. Thus, suvorexant provided in step (a) may be present in crystalline form I or II or may represent a mixture of form I or II. Preferably, suvorexant is provided in polymorphic form I or II, as described in WO 2012/148553 A1. Thus, the present invention also relates to a process for preparing a solid dispersion and a solid dispersion obtained or obtainable by the above-described method, wherein in step (a) crystalline suvorexant, preferably in polymorphic form I or II, is provided.

Alternatively, suvorexant in step (a) is provided in amorphous form. No specific restrictions exist how the amorphous suvorexant is prepared. Preferably, the amorphous suvorexant is prepared from suvorexant of which at least 95 weight-%, preferably at least 99 weight-%, more preferably at least 99.9 weight-% are present in at least one crystalline form, preferably in crystalline form I and/or II. Preferably, the crystalline suvorexant is dissolved in at least one solvent, and the obtained solution is subjected to at least one treatment stage from which the amorphous suvorexant is obtained. Regarding the at least one solvent, no specific restrictions exist. Preferably, the at least one solvent is selected from the group consisting of C1-C3 ketones, C1-C2 halogenated hydrocarbons, C1-C4 alcohols, C2-C6 ethers, C3-C5 esters, and a combination of two or more thereof, more preferably from the group consisting of C1-C2 halogenated hydrocarbons, more preferably dichloromethane. Regarding the at least one treatment stage from which the amorphous suvorexant is obtained, no specific restrictions exist, provided that the amorphous suvorexant is obtained. Preferably, the treatment stage comprises subjecting at least a portion of the solution of the suvorexant to lyophilization or rapid-drying, preferably to rapid-drying, wherein the rapid-drying preferably comprises at least one atomization process, and is more preferably carried out by spray-drying or spray-granulation, preferably by spray-drying. Prior to the rapid-drying, the solution of the suvorexant can be concentrated with respect to the suvorexant content, for example by filtration, centrifugation, evaporation, adding suvorexant to the solution, or a combination of two or more of these methods.

Therefore, besides the process for preparing a solid dispersion, the present invention also relates to a process, wherein suvorexant is prepared by a method comprising (a1) providing suvorexant of which at least 95 weight-%, preferably at least 99 weight-%, more preferably at least 99.9 weight-% are present in at least one crystalline form;

(a2) dissolving at least a portion of the suvorexant provided according to (a1) in at least one solvent, preferably in dichloromethane, thereby obtaining a solution comprising the suvorexant;

(a3) subjecting at least a portion of the solution obtained according to (a2), optionally after concentrating, to lyophilisation or rapid-drying, preferably rapid-drying, obtaining the suvorexant of which at least 95 weight-%, preferably at least 99 weight-%, more preferably at least 99.9 weight-% are present in its amorphous form.

The preferred rapid-drying method, the spray-drying, is not subjected to specific restrictions provided that the amorphous suvorexant is obtained. Preferably, the inlet temperature used is in the range of from 50 to 90° C., more preferably in the range of from 55 to 75° C. Preferably, the outlet temperature used is in the range of from 20 to 70° C., more preferably in the range of from 30 to 50° C.

Generally, the present invention also relates to a process for the preparation of suvorexant of which at least 95 weight-%, preferably at least 99 weight-%, more preferably at least 99.9 weight-% are present in its amorphous form, comprising (a1) providing suvorexant of which at least 95 weight-%, preferably at least 99 weight-%, more preferably at least 99.9 weight-% are present in at least one crystalline form;

(a2) dissolving at least a portion of the suvorexant provided according to (a1) in at least one solvent, thereby obtaining a solution comprising the suvorexant;

(a3) subjecting at least a portion of the solution obtained according to (a2), optionally after concentrating, to rapid-drying, obtaining the suvorexant of which at least 95 weight-%, preferably at least 99 weight-%, more preferably at least 99.9 weight-% are present in its amorphous form;

wherein the at least one solvent according to (a2) is preferably selected from the group consisting of water, C1-C3 ketones, C1-C2 halogenated hydrocarbons, C1-C4 alcohols, C2-C6 ethers, C3-C5 esters, and a combination of two or more thereof, more preferably from the group consisting of water, C1-C4 alcohols, C1-C3 ketones, and a combination of two or more thereof, wherein more preferably, the at least one solvent comprises, more preferably consists of, C1-C2 halogenated hydrocarbons, preferably dichloromethane.

Further, the present invention also relates to a process for preparing a solid dispersion comprising suvorexant or salt thereof in amorphous form and at least one pharmaceutically acceptable matrix compound, the process comprising (a) providing suvorexant or a salt thereof (b) dissolving or dispersing suvorexant provided in (a) and the at least one matrix compound in a solvent to form a mixture, optionally in the presence of a surfactant, preferably a nonionic surfactant (c) removing at least part, preferably essentially all, of the solvent to give the solid dispersion, and wherein the at least one matrix compound is (i) a polymer and wherein the solid dispersion contains the suvorexant or salt thereof in an amount of at least 50 weight-% based on the combined weight of the suvorexant or salt thereof and the at least one matrix compound, or (ii) a silicon-based inorganic adsorbent, wherein step (a) comprises (a1) providing suvorexant of which at least 95 weight-%, preferably at least 99 weight-%, more preferably at least 99.9 weight-% are present in at least one crystalline form;

(a2) dissolving at least a portion of the suvorexant provided according to (a1) in at least one solvent, preferably in dichloromethane, thereby obtaining a solution comprising the suvorexant;

(a3) subjecting at least a portion of the solution obtained according to (a2), optionally after concentrating, to lyophilisation or rapid-drying, preferably rapid-drying, obtaining the suvorexant of which at least 95 weight-%, preferably at least 99 weight-%, more preferably at least 99.9 weight-% are present in its amorphous form.

Step (b)

In step (b), suvorexant provided in step (a) is preferably dissolved or dispersed together with the at least one matrix compound in a suitable solvent. Both components may be dissolved or dispersed together or subsequently.

The term "a suitable solvent" as used herein refers to a solvent or solvent mixture in which both suvorexant antagonist and the at least one matrix compound have adequate solubility or may be suitably dispersed. The term "adequate solubility" is denoted to mean a solubility at room temperature of greater than about 10 mg/ml. In case suvorexant and the polymer require different solvents to obtain the desired solubility, preferably a mixture of solvents is used. In this case, suvorexant may be dissolved in at least one solvent to give a mixture comprising the at least one solvent and the orexin receptor antagonist. Likewise, the polymer may be dissolved in at least one further solvent to give a mixture comprising the polymer and the at least one further solvent. Both mixtures may then be mixed together.

Suvorexant and polymer may be dissolved or dispersed, together or subsequently, in the suitable solvent (including solvent mixtures).

Examples of suitable solvents include, but are not limited to, water, C1-C3 ketones, C1-C2 halogenated hydrocarbons, C3-C4 alcohols, C2-C6 ethers, C3-C5 esters, and a combination of two or more thereof, more preferably from the group consisting of C1-C3 ketones, and a combination of two or more thereof More preferably, the solvent is selected from the group consisting of dichlormethane, chloroform, ethanol, methanol, THF, 2-propanol, ethyl acetate, acetone, water or mixtures thereof. Preferably, the solvent is selected from the group consisting of dichlormethane, THF, methyl THF and mixtures of two or more thereof.

In this case where the at least one matrix compound is selected from the group consisting of silicon-based inorganic adsorbents and a combination of two or more thereof, it is preferred that the process comprises dispersing the at least one matrix compound in the solution comprising the suvorexant.

Consequently, solvents are preferred in which suvorexant can be dissolved and the at least one silicon-based inorganic adsorbent can be dispersed. Preferably, the at least one suitable solvent is selected from the group consisting of water, C1-C3 ketones, C1-C2 halogenated hydrocarbons, C3-C4 alcohols, C2-C6 ethers, C3-C5 esters, and a combination of two or more thereof, more preferably from the group consisting of C1-C3 ketones, and a combination of two or more thereof.

Regarding the weight ratio of suvorexant and the at least one silicon-based inorganic adsorbent relative to the at least one solvent, no specific restrictions exist provided that the finally obtained mixture is a mixture wherein the at least one silicon-based inorganic adsorbent is dispersed in a solution of the suvorexant in the at least one solvent, which mixture can be subjected to the subsequent step (c). Preferably, the weight ratio of suvorexant or salt thereof plus the at least one silicon-based inorganic adsorbent, preferably suvorexant or salt thereof plus the at least one silica, relative to the at least one solvent, preferably the dichloromethane, is in the range of from 0.01:1 to 0.3:1, preferably in the range of from 0.02:1 to 0.2:1, more preferably in the range of from 0.05:1 to 0.2:1. Also preferably, the weight ratio of suvorexant plus the at least one silicon-based inorganic adsorbent, preferably suvorexant plus the at least one silicate, preferably the aluminosilicates preferably comprising at least one alkali metal element and/or at least one alkaline earth metal element, more preferably at least one alkaline earth metal element, more preferably magnesium, relative to the at least one solvent, preferably the dichloromethane, is in the range of from 0.01:1 to 0.3:1, more preferably in the range of from 0.02:1 to 0.2:1, more preferably in the range of from 0.05:1 to 0.2:1.

To accelerate and/or improve the solution process of suvorexant in the at least one solvent, suitable methods can be applied. For example, the solution process can be influenced by choosing suitable temperatures, by stirring, and/or by subjecting the respective mixtures to sonication, wherein these methods can be applied during the entire or one or more parts of the mixing process.

Preferably, the dispersion of the at least one silicon-based inorganic adsorbent, preferably selected from the group consisting of silica, silicates, and a combination of two or more thereof, in the solution of suvorexant in the at least one solvent, is prepared at a temperature in the range of from 10 to 40° C., more preferably in the range of from 15 to 35° C., more preferably in the range of from 20 to 30° C., preferably at ambient pressure.

The solution obtained in step (b) may be directly used in step (c) of the method according to the invention. According to a preferred embodiment, the solution formed is purified before used in step (c). The term "purified" in this context means e.g. that non-dissolved particles, such as non-dissolved polymer and/or non-dissolved orexin receptor antagonist, may be removed by suitable methods known to those skilled in the art such as centrifugation, filtration, ultrafiltration or the like. Preferably, the solution in step (b) is filtrated prior to step (c).

Thus, the present invention also relates to a process, as described above, the process comprising (a) providing suvorexant or a salt or a solvent thereof, wherein the suvorexant is preferably crystalline, (b) dissolving or dispersing suvorexant provided in step (a) and the at least one matrix compound in a solvent, optionally in the presence of a surfactant, preferably a nonionic surfactant, to form a solution, filtrating the solution, and (c) removing at least part, preferably essentially all, of the solvent to give the solid dispersion.

Step (c)

In step (c) of the above described method, at least part, preferably essentially all, of the solvent is removed. "Essentially all" is denoted to mean that at least 95% by weight, preferably at least 96% by weight, more preferably at least 97% by weight, more preferably at least 98% by weight, more preferably at least 99% by weight, more preferably at least 99.9% by weight, more preferably all of the solvent present in the solution according to step (b) is removed in step (c).

Preferably, the solid dispersion obtained or obtainable by this process thus comprises less than 5% by weight, more preferably less than 4% by weight, more preferably less than 3% by weight, more preferably less than 2% by weight, more preferably less than 1% by weight, more preferably less than 0.1% by weight, based on the total weight of the solid dispersion, of the solvent. Most preferably, all of the solvent present in the solution is removed to give the solid dispersion.

The removal of the solvent may be carried out by any suitable method known to those skilled in the art such as evaporation, lyophilisation, melt extrusion, drum drying, freeze drying or other solvent removal processes. Preferably, the solvent is removed by spray drying or evaporation. Spray drying is a process well known to those skilled in the art for preparing solid dispersions. In such a spray drying process, the solution is pumped through an atomizer into a drying chamber thereby removing the solvent to form the solid dispersion. A drying process uses hot gases, such as air, nitrogen, nitrogen-enriched air or argon, to dry the particles. The solution can be atomized by conventional means well known in the art, such as a two-fluid sonication nozzle and a two-fluid non-sonication nozzle.

Preferably, the solvent is removed by evaporation, such as by evaporation under reduced pressure. Preferably, the pressure in step (c) is in the range of from 50 to 450 mbar, more preferably in the range of from 50 to 250 mbar, more preferably in the range of from 50 to 200 mbar.

The temperature during evaporation may be varied or held essentially constant and is preferably in the range of from 20 to 40° C., more preferably in the range of from 25 to 40° C., and most preferably in the range of from 35 to 40° C.

As also described above, the present invention also relates to a process for preparing a solid dispersion comprising suvorexant or a salt thereof in amorphous form and at least one pharmaceutically acceptable matrix compound, the process comprising
(a') providing suvorexant or a salt thereof
(b') mixing the suvorexant provided in (a') and the at least one matrix compound to form a mixture
(c') milling the mixture according to (b')
to give the solid dispersion, and wherein the matrix compound is
(i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
(ii) a silicon-based inorganic adsorbent.

Step (a')

The provision of suvorexant may be carried out by any method known to the person skilled in the art, such as, e.g., the methods described in WO 2012/148553 A1. Suvorexant may be provided in any form, such as in crystalline or in amorphous form or as a mixture of crystalline and amorphous form. Preferably, the compound in step (a) is provided in crystalline form such as described in WO 2012/148553 A1. Thus, suvorexant provided in step (a) may be present in crystalline form I or II or may represent a mixture of form I or II. Preferably, suvorexant is provided in polymorphic form I or II, as described in WO 2012/148553 A1.

Thus, the present invention also relates to a process for preparing a solid dispersion and a solid dispersion obtained or obtainable by the above-described method, wherein in step (a') crystalline suvorexant, preferably in polymorphic form I or II, is provided.

Alternatively, suvorexant in step (a) is provided in amorphous form. No specific restrictions exist how the amorphous suvorexant is prepared. Full reference is made to the possible and preferred preparations disclosed above in the context of step (a).

Further, the present invention also relates to a process for preparing a solid dispersion comprising suvorexant or salt thereof in amorphous form and at least one pharmaceutically acceptable matrix compound, the process comprising
(a') providing suvorexant or a salt thereof
(b') mixing the suvorexant provided in (a') and the at least one matrix compound to form a mixture
(c') milling the mixture according to (b')
to give the solid dispersion, and wherein the matrix compound is
(i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
(ii) a silicon-based inorganic adsorbent,
wherein step (a') comprises
(a1) providing suvorexant of which at least 95 weight-%, preferably at least 99 weight-%, more preferably at least 99.9 weight-% are present in at least one crystalline form;
(a2) dissolving at least a portion of the suvorexant provided according to (a1) in at least one solvent, preferably in dichloromethane, thereby obtaining a solution comprising the suvorexant;
(a3) subjecting at least a portion of the solution obtained according to (a2), optionally after concentrating, to lyophilisation or rapid-drying, preferably rapid-drying, obtaining the suvorexant of which at least 95 weight-%, preferably at least 99 weight-%, more preferably at least 99.9 weight-% are present in its amorphous form.

Step (b')

In step (b'), suvorexant provided in step (a') is preferably mixed with the suvorexant provided in (a') and the at least one matrix compound to form a mixture.

Preferably, the mixing is carried out at a temperature in the range of from 0 to 50° C., more preferably of from 5 to 45° C., more preferably of from 10 to 40° C., more preferably of from 15 to 35° C., more preferably of from 20 to 30° C. Preferably, the mixing is carried out at an absolute pressure in the range of from 500 mbar to 5 bar, more preferably of from 750 mbar to 2 bar, more preferably of from 900 mbar to 1.5 bar, more preferably of from 0.95 to 1.05 bar.

Preferably, according to (b'), no components other than the suvorexant provided according to (a') and the at least one matrix compound are mixed. Therefore, it is preferred that at least 99 weight-%, more preferably at least 99.5 weight-%, more preferably at least 99.9 weight-% of the mixture according to (c') consist of the suvorexant provided in (a') and the at least one matrix compound. It is also preferred that according to (b'), the suvorexant provided according to (a') and the at least one matrix compound are mixed in dry state. Preferably, the mixture according to (b') does not contain a solvent selected from the group consisting of dichloromethane, THF, ethanol and mixtures of two or more thereof, more preferably does not contain an organic solvent, more preferably does not contain a solvent.

Step (c')

It is preferred that the milling of the mixture according to (c') is carried out by a dry milling process. Milling machines known in the art may be used, preferably various types of ball mills. One example of a ball mill is the Retsch mill (Retsch GmbH, Germany), which is a oscillating ball mill. The milling time when using a Retsch mill depends on the size of the mill, the speed of rotation and the type and amount of feed material. The influence of these variables are known in the art and the invention may be worked over a broad range of these variables. Typical milling periods range from about 10 to about 120 minutes for a lab scale equipment (25 ml milling cell), preferably from 20 to 40 minutes. Milling frequencies are typically in a range from 20 to 35 Hz, preferably from 25 to 30 Hz for a lab scale equipment. These settings may require adaptions when equipment of larger scale is used.

Pharmaceutical Composition

In another aspect of the invention, the present invention relates to a pharmaceutical composition comprising a solid dispersion as described above or a solid dispersion obtained or obtainable by the above-described method. The pharmaceutical composition preferably comprises the solid dispersion as key ingredient together with at least one further excipient in addition to the at least one matrix compound present in the solid dispersion. The at least one further excipient may be included in the solid dispersion or may be subsequently added to or mixed with the dispersion. Preferably, the pharmaceutical composition comprises no further suvorexant in addition to the suvorexant present in the solid dispersion. Thus, preferably, at least 80% by weight, more preferably at least 85% by weight, more preferably at least 90% by weight, more preferably at least 95% by weight, more preferably at least 96% by weight, more preferably at least 97% by weight, more preferably at least 98% by weight, more preferably at least by weight 99% by weight, more preferably at least 99.9% by weight, more preferably all of the suvorexant present in the pharmaceutical composition is present in amorphous form.

Suitable pharmaceutical excipient include, but are not limited to, carriers, fillers, diluents, lubricants, sweeteners, stabilizing agents, solubilizing agents, antioxidants and preservatives, flavoring agents, binder, colorants, osmotic agents preservatives, buffers, surfactants, granulating and disintegrating agents and combinations thereof.

Examples of diluents include, without limitation, calcium carbonate, sodium carbonate, lactose, calcium phosphate, microcrystalline cellulose, mannitol, starch, sodium phosphate or the like.

Examples for granulating and disintegrating agents are corn starch, alginic acid, sodium starch glycolate, crospovidone, croscarmellose sodium and the like.

The pharmaceutical composition of the present invention may optionally comprise one or more surfactants, which may be ionic or nonionic surfactants. The surfactants can increase the rate of dissolution by facilitating wetting, thereby increasing the maximum concentration of dissolved drug. The surfactants may also make the dispersion easier to process. Surfactants may also stabilize the amorphous dispersions by inhibiting crystallization or precipitation of the drug by interacting with the dissolved drug by such mechanisms as complexation, formation of inclusion complexes, formation of micelles, and adsorption to the surface of the solid drug. Suitable surfactants include cationic, anionic, and nonionic surfactants.

These include for example fatty acids and alkyl sulfonates; cationic surfactants such as benzalkonium chloride); anionic surfactants, such as dioctyl sodium sulfosuccinate and sodium lauryl sulfate (sodium dodecyl sulfate); sorbitan fatty acid esters; Vitamin E TPGS; polyoxyethylene sorbitan fatty acid esters; polyoxyethylene castor oils and hydrogenated castor oils such as Cremophor RH-40 and Cremopher EL; Liposorb P-20, Capmul POE-0, and natural surfactants such as lecithin and other phospholipids and mono- and diglycerides.

Thus, the present invention also relates to a pharmaceutical composition as described above, wherein the composition comprises one or more surfactants selected from the group consisting of anionic surfactants and nonionic surfactants.

Preferably, the pharmaceutical composition comprises one or more surfactants selected from sodium dodecyl sulfate and one or more nonionic surfactants selected from (a) sorbitan fatty acid esters, (b) polyoxyethylene sorbitan fatty acid esters, (c) polyoxyethylene castor oils, (d) polyoxyethylene hydrogenated castor oils, and (e) vitamin E TPGS; and mixtures thereof.

Examples of carriers include, without limitation, solvents, saline, buffered saline, dextrose, water, glycerol, ethanol, propylene glycol, polysorbate 80 (Tween® 80), poly(ethylene)glycol 300 and 400 (PEG 300 and 400), PEGylated castor oil (e.g. Cremophor® EL), poloxamer 407 and 188, hydrophobic carriers, fat emulsions, lipids, PEGylated phopholids, polymer matrices, biocompatible polymers, lipospheres, vesicles, particles, and liposomes, or combinations thereof.

Examples of osmotic agents include sodium chloride, glycerol, sorbitol, xylitol, glucose, or combinations thereof.

Binders can include acacia gum, starch, gelatin, sucrose, polyvinylpyrrolidone (Povidone), sorbitol, or tragacanth methylcellulose, sodium carboxymethylcellulose, hydroxypropyl methylcellulose, ethylcellulose, or combinations thereof.

Examples of fillers can include calcium phosphate, glycine, lactose, maize-starch, sorbitol, sucrose, or combinations thereof.

Exemplary lubricants include magnesium stearate or other metallic stearates, stearic acid, polyethylene glycol, waxes, oils, silica and colloidal silica, silicon fluid, talc, or combinations thereof.

As flavoring agent those flavoring agents approved by the FTA for use in sweets and pharmaceuticals, foods, candies and beverages or the like are preferred. Preferably, these flavoring agents impart flavors such as grape, cherry, citrus, peach, strawberry, bubble gum, peppermint or others. Peppermint, methyl salicylate, orange flavoring and the like are mentioned by way of examples.

The pharmaceutical composition of the present invention preferably contains a therapeutically effective amount of suvorexant. The term "therapeutically effective amount" as used herein refers to an amount of suvorexant present in the solid dispersion or pharmaceutical composition being administered that is sufficient to prevent the development of or alleviate to some extent one or more of the symptoms of the sleep disorder.

The pharmaceutical composition of the present invention is preferably administered orally to patients, which include, but is not limited to, mammals, for example humans, in the form of, for example, a tablet, pills, granules or the like. It is also apparent that the pharmaceutical composition of the present invention can be administered with other therapeutic and/or prophylactic agents and/or medications that are not medically incompatible therewith.

Preferably, for example, any of the pharmaceutical compositions of the present invention are in the form of a tablet. Generally, the content of the tablet with regard to the amorphous suvorexant, relative to the total weight of the tablet, is at least 5% by weight. Preferred ranges may be of from 5 to 95% by weight or from 5 to 85% by weight or from 5 to 75% by weight or from 5 to 65% by weight or from 5 to 55% by weight or from 5 to 45% by weight or from 5 to 35% by weight or from 5 to 25% by weight or from 5 to 15% by weight, such as from 5 to 10% by weight or from 10 to 15% by weight.

The tablet may comprise at least one excipient. Generally, there are no specific restrictions concerning the chemical nature of these excipients provided that the excipient or mixture of excipients comprised in the tablet is pharmaceutically acceptable, and that suvorexant is stable in its amorphous form in the tablet. A pharmaceutically acceptable excipient is any excipient which is relatively non-toxic and innocuous to a patient at concentrations consistent with effective activity of the suvorexant so that any side effects ascribable to the excipient do not vitiate the beneficial effects of the suvorexant. Therefore, according to the present invention, excipients are, for example, disintegrants, binders, lubricants, fillers, plasticizers, surfactants and wetting agents, film-forming agents and coating materials, sweeteners, flavoring agents, and coloring agents such as example pigments. Other excipients known in the field of pharmaceutical compositions may also be used.

Suitable disintegrants may include, but are not limited to, carboxymethylcellulose calcium, carboxymethylcellulose sodium, croscarmellose (crosslinked carboxymethylcellulose) sodium, cross-linked polyvinylpyrrolidone, crospovidone (cross-linked povidone, a synthetic cross-linked homopolymer of N-vinyl-2-pyrrolidone), alginic acid, microcrystalline cellulose (such as refined wood pulp derived from alpha cellulose), hydroxypropyl cellulose, low substituted hydroxypropyl cellulose, polacrilin potassium, sodium alginate, sodium starch glycolate, partially hydrolysed starch, sodium carboxymethyl starch, and starch.

Suitable binders may include, but are not limited to, hydroxypropyl cellulose, hypromellose (hydroxypropyl methylcellulose, HPMC), microcrystalline cellulose, acacia, alginic acid, carboxymethylcellulose, ethylcellulose, methylcellulose, hydroxyethylcellulose, ethylhydroxyethylcellulose, polyvinyl alcohol, polyacrylates, carboxymethylcellulose calcium, carboxymethylcellulose sodium, compressible sugar, ethylcellulose, gelatin, liquid glucose, methylcellulose, polyvinyl pyrrolidone and pregelatinized starch.

Suitable lubricants may include, but are not limited to, calcium stearate, magnesium stearate, mineral oil, stearic acid, fumaric acid, sodium stearylfumarate, zinc stearate and polyethylene glycol.

Suitable fillers may include, but are not limited to, dibasic calcium phosphate, kaolin, microcrystalline cellulose, silicated microcrystalline cellulose, dicalcium phosphate, tricalcium phosphate, magnesium trisilicate lactose such as example the anhydrous form or the hydrate form such as the monohydrate form, sugars such as dextrose, maltose, saccharose, glucose, fructose or maltodextrine, sugar alcohols such as mannitol, maltitol, sorbitol, xylitol, powdered cellulose, precipitated calcium carbonate, sodium carbonate, sodium phosphate and starch.

Suitable surfactants and wetting agents may include, but are not limited to, heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates, for example polysorbate 20, polysorbate 40, polysorbate 60 or polysorbate 80, sorbitan monopalmitate, sodium salts of fatty alcoholsulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides.

Suitable film-forming agents and coating materials may include, but are not limited to, liquid glucose, hydroxyethyl cellulose, hydroxypropyl cellulose, hydroxypropyl methylcellulose (hypromellose, HPMC), methylcellulose, ethylcellulose, cellulose acetate phthalate, shellac, polyvinylpyrrolidone, copolymers of vinylpyrrolidone and vinylacetate such as Kollidon® VA64 BASF, copolymers of acrylic and/or methacrylic acid esters with trimethylammoniummethylacrylate, copolymers of dimethylaminomethacrylic acid and neutral methacrylic acid esters, polymers of methacrylic acid or methacrylic acid esters, copolymers of acrylic acid ethylester and methacrylic acid methyl ester, and copolymers of acrylic acid and acrylic acid methylester.

Suitable plasticizers may include, but are not limited to, polyethylene glycol, diethyl phthalate and glycerol.

Suitable coloring agents may include, but are not limited to, pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide.

Suitable further commonly used excipients which may be used may include, but are not limited to, acidifying agents such as acetic acid, citric acid, fumaric acid, hydrochloric acid and nitric acid; alkalizing agents such as ammonia solution, ammonium carbonate, diethanolamine, monoethanolamine, potassium hydroxide, sodium borate, sodium carbonate, sodium hydroxide, triethanolamine and trolamine; adsorbents such as powdered cellulose and activated charcoal; stabilizers and antioxidants such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate and sodium metabisulfite; binding materials such as block polymers, natural and synthetic rubber, polyacrylates, polyurethanes, silicones, polysiloxanes and styrene-butadiene copolymers; buffering agents such as potassium metaphosphate, dipotassium phosphate, sodium acetate, sodium citrate anhydrous and sodium citrate hydrates; encapsulating agents such as gelatin, starch and cellulose derivates; flavorants, masking agents and odors such as anise oil, cinnamon oil, cocoa, menthol, orange oil, peppermint oil and vanillin; humectants such as glycerol, propylene glycol and sorbitol; sweeteners such as aspartame, dextrose, glycerol, mannitol, propylene glycol, saccharin sodium, sorbitol and sucrose; anti-adherents such as magnesium stearate and talc; direct compression excipients such as dibasic calcium phosphate, lactose and microcrystalline cellulose; tablet polishing agents such as carnauba wax and white wax.

Preferably excipients include one or more of microcrystalline cellulose; lactose, preferably lactose hydrate, more preferably lactose monohydrate; croscarmellose, preferably croscarmellose sodium; stearate, preferably magnesium stearate.

For the preparation of the tablet, a solid dispersion of the present invention can be employed which is prepared including dissolving the suvorexant in a solvent and suitably removing the solvent, as described herein in the context of the process comprising steps (a), (b) and (c). Further, for the preparation of the tablet, a solid dispersion of the present invention can be employed which is prepared including milling as described herein in the context of the process comprising steps (a'), (b') and (c'). Yet further, for the preparation of the tablet, a combination of these solid dispersions can be employed.

The tablet may be an uncoated tablet, a coated tablet, an effervescent tablet, a soluble tablet, a dispersible tablet, an orodispersible tablet, a tablet for use in the mouth, or a chewable tablet.

The solid dispersion described above may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with the solid dispersion of the present invention.

Use

The solid dispersion, described above, or the pharmaceutical composition described above is useful in a method of antagonizing orexin receptor activity. Thus, the present invention also describes the solid dispersion, described above, or a pharmaceutical composition, as described above for use as antagonists of orexin receptor activity. In particular, the solid dispersion, described above, or the pharmaceutical composition, described above is used for treating, preventing, ameliorating, controlling or reducing the risk of a variety of neurological and psychiatric disorders associated with orexin receptors, in particular for enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof.

In particular, the solid dispersion, described above, or the pharmaceutical composition, described above is used for treating in treating or preventing of a sleep disorder, in particular for enhancing the quality of sleep or for treating insomnia in a mammalian patient. In particular, the solid dispersion, described above, or the pharmaceutical composition, described above is used for treating or controlling obesity in a mammalian patient.

As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

Further, the present invention also relates to a method for enhancing the quality of sleep in a mammalian patient in need thereof which comprises administering the pharmaceutical composition to the patient. Further, the present invention also relates to method for treating insomnia in a mammalian patient in need thereof which comprises administering the pharmaceutical composition, described above, to the patient. Further, the present invention also relates to a method for treating or controlling obesity in a mammalian patient in need thereof which comprises administering the pharmaceutical composition, described above, to the patient.

The dosage of suvorexant in the compositions of this invention may be varied, however, it is necessary that the amount of suvorexant be such that a suitable dosage form is obtained. The dosage regimen will be determined by the attending physician and other clinical factors. It is well known in the medical art that the dosage for anyone patient depends upon many factors including the patient's size, body surface area, age, sex, time and route of administration, general health and other drugs being administered concurrently. Efficacy can be monitored by periodic assessment. Suvorexant may be administered to patients (animals and human) in need of such treatment in dosages that will provide optimal pharmaceutical efficacy. A typical dosage can be, for example, in the range of 10 to 80 mg, such as 10, 20, 40 or 80 mg.

By way of example, the following particularly preferred embodiments of the invention and combinations of embodiments as indicate by the respective dependencies and references are mentioned:

1. A solid dispersion comprising suvorexant ([7R)-4-(5-chloro-1,3-benzoxazol-2-yl)-7-methyl-1,4-diazepan-1-yl][5-methyl-2-(2H-1,2,3-triazol-2-yl)phenyl]methanone) or a salt thereof in amorphous form and at least one pharmaceutically acceptable matrix compound, wherein the at least one matrix compound is
   (i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
   (ii) a silicon-based inorganic adsorbent.

2. The solid dispersion according to embodiment 1, wherein at least 80% by weight, more preferably at least 90% by weight, more preferably all of the suvorexant or salt thereof present in the solid dispersion is present in amorphous form.

3. The solid dispersion according to embodiment 1 or 2, wherein in the adsorption-desorption isotherm of the at least one matrix compound in (ii), the mass difference $\Delta m$(adsorption) between 50 and 90% relative humidity at 25° C. is greater than or equal to 40%, determined according to dynamic vapor sorption measurement.

4. The solid dispersion according any one of embodiments 1 to 3, wherein in the adsorption-desorption isotherm of the at least one matrix compound in (ii), the mass difference $\Delta m$(adsorption) between 0 and less than 50% relative humidity at 25° C. is less than or equal to 20%, determined according to dynamic vapor sorption measurement.

5. The solid dispersion any one of embodiments 1 to 4, wherein the polymer in (i) is a cellulose derivative or a polyvinyl caprolactam polyvinyl acetate polyethylene glycol graft polymer.

6. The solid dispersion according to any one of embodiments 1 to 5 wherein the polymer in (i) is polyvinyl caprolactam-polyvinyl acetate-polyethylene glycol, preferably soluplus.

7. The solid dispersion according to any one of embodiments 1 to 6, wherein the polymer in (i) is a cellulose derivative selected from the group consisting of hydroxyalkylalkylcelluloses and a mixture of two or more thereof, more preferably a hydroxypropylmethylcellulose or a hydroxymethylcellulose.

8. The solid dispersion according to embodiment 7, wherein the cellulose derivative has a degree of substitution (DS) in the range of from 0.3 to 2.8, preferably in the range of from 0.6 to 2.5, more preferably in the range of from 1.0 to 2.3, more preferably in the range of from 1.3 to 2.0.

9. The solid dispersion according to any one of embodiments 1 to 8, wherein the solid dispersion in (i) contains the suvorexant or the at least one salt thereof in an amount of at least 60 weight-%, preferably at least 80% by weight, more preferably in the range of from 80 to 95% weight-%, based on the combined weight of the suvorexant or the at least one salt thereof and the at least one matrix compound.

10. The solid dispersion according to any one of embodiments 1 to 4, wherein in the adsorption-desorption isotherm of the silicon-based inorganic adsorbent in (ii), the mass difference $\Delta m$(desorption) at 75% relative humidity and 25° C. is greater than or equal to the mass difference $\Delta m$(adsorption) at 75% relative humidity and 25° C., determined according to dynamic vapor sorption measurement.

11. The solid dispersion according to any one of embodiments 1 to 4 or 10, wherein the silicon-based inorganic adsorbent in (ii) has a pH in the range of from 6.0 to 9.0, preferably in the range of from 6.5 to 8.5, more preferably in the range of from 6.8 to 8.0.

12. The solid dispersion according to any one of embodiments 1 to 4 or 10 or 11, wherein the at least one silicon-based inorganic adsorbent in (ii) has an oil adsorbance in the range of from 1.0 to 5.0 ml/g, preferably in the range of from 2 to 3.5 ml/g.

13. The solid dispersion according to any one of embodiments 1 to 4 or 10 to 12, wherein the at least one silicon-based inorganic adsorbent in (ii) has a bulk density in the range of from 0.05 to 0.25 g/ml, preferably in the range of from 0.10 to 0.22 g/ml, more preferably in the range of from 0.10 to 0.16 g/ml.

14. The solid dispersion according to any one of embodiments 1 to 4 or 10 to 13, wherein the silicon-based inorganic adsorbent in (ii) is selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium, wherein more preferably, at least 90 weight-%, more preferably at least 95 weight-%, more preferably at least 99 weight-% of the at least one silicon-based inorganic adsorbent are present in amorphous form.

15. The solid dispersion according to any one of embodiments 1 to 4 or 10 to 14, wherein the solid dispersion in (ii) contains the suvorexant or the at least one salt thereof in an amount in the range of from 10 to 70 weight-%, more preferably in the range of from 20 to 65% by weight, more preferably in the range of from 30 to 60% by weight, more preferably in the range of from 35 to 55% by weight, more preferably in the range of from 40 to 55% by weight, more preferably in the range of from 45 to 55% by weight, based on the combined weight of the suvorexant or the at least one salt thereof and the at least one matrix compound.

16. The solid dispersion according to any one of embodiments 1 to 15, wherein at least 99 weight-%, preferably at least 99.5 weight-%, more preferably at least 99.9 weight-% of the solid dispersion consist of suvorexant or a salt thereof, the at least one matrix compound and optionally at least one solvent.

17. The solid dispersion according to any one of embodiments 1 to 16, consisting of suvorexant or a salt thereof, the at least one matrix compound and at least one solvent.

18. The solid dispersion according to any one of embodiments 1 to 16, consisting of suvorexant or a salt thereof and the at least one matrix compound.

19. The solid dispersion according to any one of embodiments 1 to 15, comprising a nonionic surfactant, preferably a block copolymer of ethylene oxide and propylene oxide, more preferably a block copolymer of ethylene oxide and propylene oxide according to the following formula:

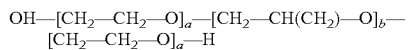

OH—[CH$_2$—CH$_2$—O]$_a$—[CH$_2$—CH(CH$_2$)—O]$_b$—[CH$_2$—CH$_2$—O]$_a$—H

20. The solid dispersion according to embodiment 19, wherein a is in the range of from 50 to 150, preferably from 60 to 130, more preferably from 70 to 110, and b is in the range of from 10 to 80, preferably of from 20 to 70, more preferably of from 30 to 60.

21. The solid dispersion according to embodiment 19 or 20, wherein a is in the range of from 75 to 85 and b is in the range of from 25 to 30.

22. The solid dispersion according to any one of embodiments 19 to 21, wherein at least 99 weight-%, preferably at least 99.5 weight-%, more preferably at least 99.9 weight-% of the solid dispersion consist of suvorexant or a salt thereof, the at least one matrix compound, the nonionic surfactant and optionally at least one solvent.

23. The solid dispersion according to any one of embodiments 19 to 22, consisting of suvorexant or a salt thereof, the at least one matrix compound, the nonionic surfactant and at least one solvent.

24. The solid dispersion according to any one of embodiments 19 to 22, consisting of suvorexant or a salt thereof, the nonionic surfactant and the at least one matrix compound.

25. A process for preparing a solid dispersion comprising suvorexant or a salt thereof in amorphous form and at least one pharmaceutically acceptable matrix compound, the process comprising
    (a) providing suvorexant or a salt thereof
    (b) dissolving or dispersing suvorexant provided in (a) and the at least one matrix compound in a solvent to form a mixture
    (c) removing at least part, preferably essentially all, of the solvent
    to give the solid dispersion, and wherein the matrix compound is
    (i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
    (ii) a silicon-based inorganic adsorbent.

26. The process according to embodiment 25, wherein in step (a) crystalline suvorexant is provided.

27. The process according to embodiment 25, wherein in step (a) crystalline form I or II of suvorexant is provided.

28. The process according to any one of embodiments 25 to 27, wherein at least 80% by weight of all suvorexant comprised in the solid dispersion is amorphous.

29. The process according to any one of embodiments 25 to 28, wherein the at least one solvent in (b) is an organic solvent, preferably a solvent selected from the group consisting of dichloromethane, THF, ethanol and mixtures of two or more thereof.

30. The process according to any one of embodiments 25 to 29, wherein the solution in (b) is filtrated prior to step (c).

31. The process according to any one of embodiments 25 to 30, wherein in step (c) the solution is evaporated, preferably at a pressure in the range of from 50 to 450 mbar.

32. A process for preparing a solid dispersion comprising suvorexant or a salt thereof in amorphous form and at least one pharmaceutically acceptable matrix compound, the process comprising
    (a') providing suvorexant or a salt thereof
    (b') mixing the suvorexant provided in (a') and the at least one matrix compound to form a mixture
    (c') milling the mixture according to (b')
    to give the solid dispersion, and wherein the matrix compound is
    (i) a polymer and wherein the solid dispersion contains the suvorexant or salt thereof in an amount of at least 50 weight-%, preferably at least 60 weight-% based on the combined weight of the suvorexant or salt thereof and the at least one matrix compound, or
    (ii) a silicon-based inorganic adsorbent.

33. The process according to embodiment 32, wherein in step (a') crystalline suvorexant is provided.

34. The process according to embodiment 33, wherein in step (a') crystalline form I or II of suvorexant is provided.

35. The process according to any one of embodiments 32 to 34, wherein at least 80% by weight of all suvorexant comprised in the solid dispersion is amorphous.

36. The process according to any one of embodiments 32 to 35, wherein at least 99 weight-%, preferably at least 99.5 weight-%, more preferably at least 99.9 weight-% of the mixture according to (c') consist of the suvorexant provided in (a') and the at least one matrix compound.
37. The process according to any one of embodiments 32 to 36, wherein according to (c'), the mixture is milled.
38. The process of any of embodiments 32 to 37, wherein according to (c'), the mixture is dry-milled.
39. A process for the preparation of suvorexant of which at least 95 weight-%, preferably at least 99 weight-%, more preferably at least 99.9 weight-% are present in its amorphous form, comprising
   (a1) providing suvorexant of which at least 95 weight-%, preferably at least 99 weight-%, more preferably at least 99.9 weight-% are present in at least one crystalline form;
   (a2) dissolving at least a portion of the suvorexant provided according to (a1) in at least one solvent, obtaining a solution comprising the suvorexant;
   (a3) subjecting at least a portion of the solution obtained according to (a2), optionally after concentrating, to rapid-drying, obtaining the suvorexant of which at least 95 weight-%, preferably at least 99 weight-%, more preferably at least 99.9 weight-% are present in its amorphous form;
   wherein the at least one solvent according to (a2) is preferably selected from the group consisting of water, C1-C3 ketones, C1-C2 halogenated hydrocarbons, C1-C4 alcohols, C2-C6 ethers, C3-C5 esters, and a combination of two or more thereof, more preferably from the group consisting of water, C1-C4 alcohols, C1-C3 ketones, and a combination of two or more thereof, wherein more preferably, the at least one solvent comprises, more preferably consists of, C1-C2 halogenated hydrocarbons, more preferably dichloromethane.
40. A solid dispersion, obtainable or obtained by the process according to any one of embodiments 25 to 31 or according to any one of embodiments 32 to 38.
41. A pharmaceutical composition comprising a solid dispersion according to any one of embodiments 1 to 24 or according to embodiment 40.
42. The pharmaceutical composition of embodiment 41, wherein the composition comprises one or more surfactants selected from the group consisting of anionic surfactants and nonionic surfactants.
43. The pharmaceutical composition of embodiment 41 or 42, wherein the composition comprises one or more surfactants selected from the group consisting of sodium dodecyl sulfate and one or more nonionic surfactants selected from the group consisting of (a) sorbitan fatty acid esters, (b) polyoxyethylene sorbitan fatty acid esters, (c) polyoxyethylene castor oils, (d) polyoxyethylene hydrogenated castor oils, and (e) vitamin E TPGS; and mixtures thereof.
44. The pharmaceutical composition of any one of embodiments 41 to 43, wherein the composition is in the form of a tablet.
45. A pharmaceutical composition comprising a solid dispersion according to any one of embodiments 1 to 24 or a pharmaceutical composition according to any one of embodiments 41 to 44, for use in treating or preventing of a sleep disorder.
46. A method for enhancing the quality of sleep in a mammalian patient in need thereof which comprises administering the pharmaceutical composition according to any one of embodiments 41 to 44.
47. A method for treating insomnia in a mammalian patient in need thereof which comprises administering the pharmaceutical composition according to any one of embodiments 41 to 44.
48. A method for treating or controlling obesity in a mammalian patient in need thereof which comprises administering to the patient the pharmaceutical composition according to any one of embodiments 41 to 44.
49. Use of a silicon-based inorganic adsorbent for stabilizing amorphous suvorexant or an amorphous salt of suvorexant in a solid dispersion and/or in a pharmaceutical composition.
50. The use of embodiment 49, wherein in the adsorption-desorption isotherm of the at least one matrix compound in (ii), the mass difference $\Delta m$(desorption) at 75% relative humidity and 25° C. is greater than or equal to the mass difference $\Delta m$(adsorption) at 75% relative humidity and 25° C., determined according to dynamic vapor sorption measurement.
51. The use of embodiment 49 or 50 for stabilizing amorphous suvorexant or an amorphous salt of suvorexant in a solid dispersion, wherein the solid dispersion contains the suvorexant or the salt thereof in an amount in the range of from 10 to 70 weight-%, more preferably in the range of from 20 to 65% by weight, more preferably in the range of from 30 to 60% by weight, more preferably in the range of from 35 to 55% by weight, more preferably in the range of from 40 to 55% by weight, more preferably in the range of from 45 to 55% by weight, based on the combined weight of the suvorexant or the salt thereof and the silicon-based inorganic adsorbent.

The present invention is further illustrated by the following examples.

EXAMPLES

I. Preparation of Solid Dispersions

Example 1: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Soluplus® as Polymer (Matrix Compound)

Figure 1:
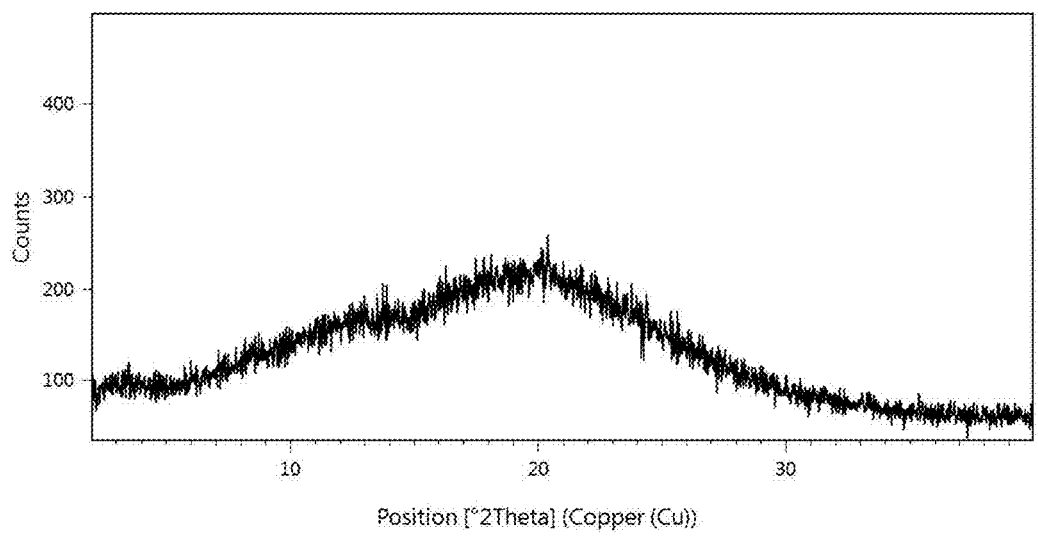
FIG. 1: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl]methanone and Soluplus® with a weight ratio of 1:1. The Y-axis shows the counts, the X-axis precision of the 2 theta angle (copper).

151 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 151 mg Soluplus® were dissolved in 10 mL dichloromethane. After filtration, the clear solution was evaporated on a rotavapor at room temperature. The foam-like residue was dried under vacuum at room temperature for 18 hours. The resulting solid dispersion was analyzed using PXRD which showed that the [(7R)-4-(5-chloro-1,3-benzoxazol-2-yl)-7-methyl-1,4-diazepan-1-yl][5-methyl-2-(2H-1,2,3-triazol-2-yl)phenyl] methanone was present in amorphous form (cf. FIG. 1).

Example 2: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Soluplus® as Polymer (Matrix Compound)

113 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 113 mg of Soluplus® were dissolved in 20 mL methyl THF. Subsequently the solvent was evaporated on a rotavapor at 40° C. and the residue was dried under vacuum for 18 hours.

Example 3: Stability of the Solid Dispersion According to Example 1

Figure 2:
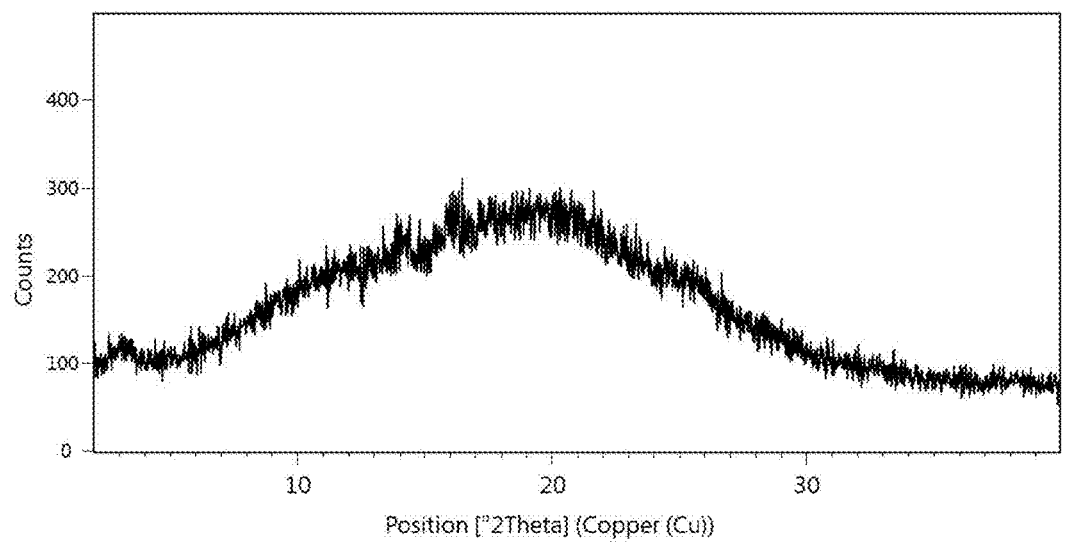
FIG. 2: shows the PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl]methanone with Soluplus®, with a weight ratio 1:1 after storage for four weeks at 40° C. and a relative humidity of 75%. X-axis: counts, Y-axis: 2 theta angles (copper).

48 mg of the solid dispersion according to Example 1 were exposed to 75% relative humidity at 40° C. for four weeks. Afterwards, the solid dispersion was analyzed using PXRD which confirmed that [(7R)-4-(5-chloro-1,3-benzoxazol-2-yl)-7-methyl-1,4-diazepan-1-yl][5-methyl-2-(2H-1,2,3-triazol-2-yl)phenyl]methanone underwent no crystallization in the presence of Soluplus® after four weeks (cf. FIG. 2).

Example 4: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with hydroxylpropylmethylcellulose Acetate Succinate as Polymer (Matrix Compound)

Figure 3:
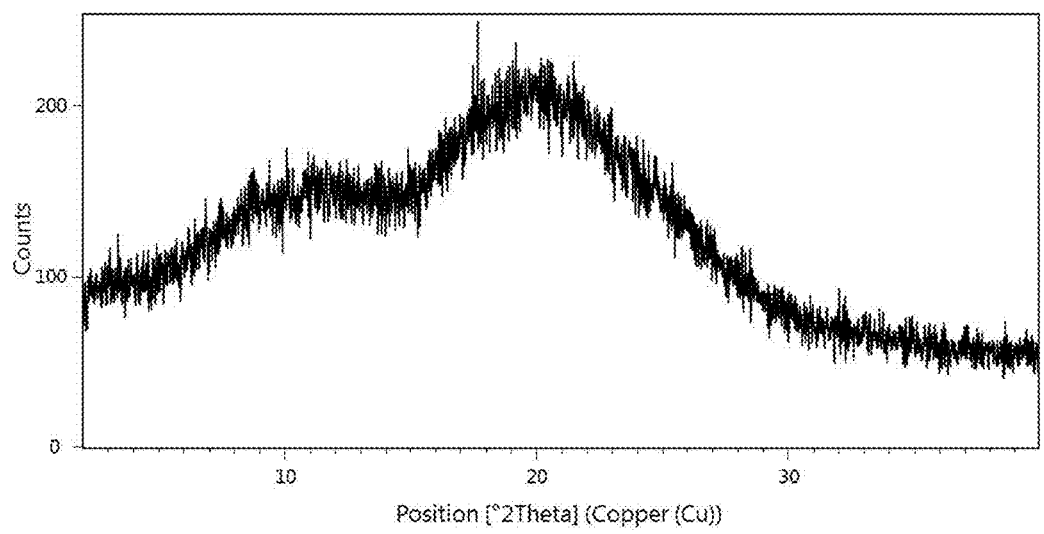
FIG. 3: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl]methanone and hydroxypropylmethylcellulose acetate succinate with a weight ratio of 1:1. The Y-axis shows the counts, the X-axis precision of the 2 theta angle (copper).

151 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 151 mg of hydroxypropylmethylcellulose acetate succinate were suspended in 40 mL CH$_2$Cl$_2$. The solvent was evaporated on a rotavapor and the residue was dried under vacuum at room temperature for 18 hours. The resulting solid dispersion was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 3).

Example 5: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with hydroxylpropylmethylcellulose Acetate Succinate as Polymer (Matrix Compound)

103 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 103 mg of hydroxypropylmethylcellulose acetate succinate were dissolved 20 ml methyl THF. Subsequently, the solvent was evaporated on a rotavapor at 40° C. and the residue was dried under vacuum for 18 hours.

Example 6: Stability of the Solid Dispersion According to Example 4

Figure 4:
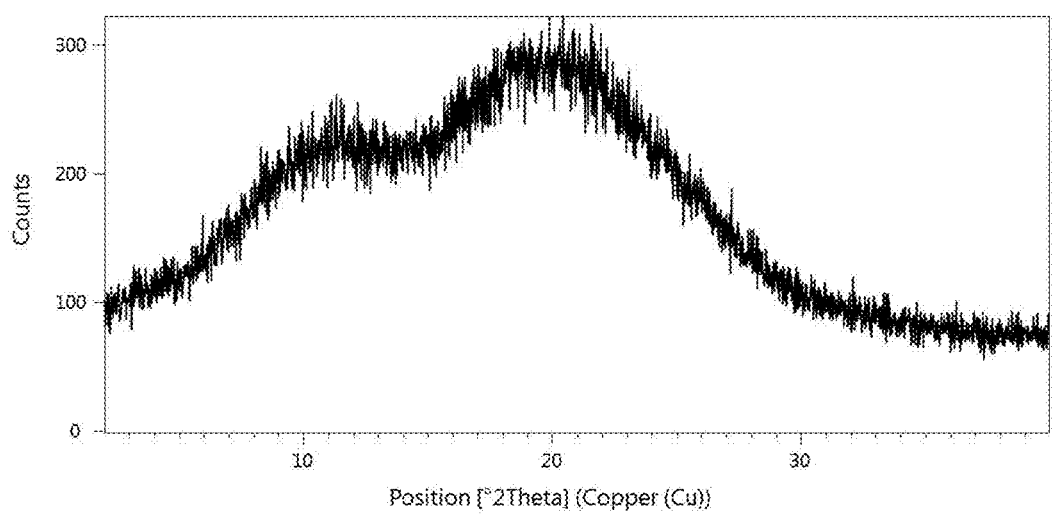
FIG. 4: shows the PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl]methanone with hydroxypropylmethylcellulose acetate succinate with a weight ratio 1:1 after storage for four weeks at 40° C. and a relative humidity of 75%. X-axis: counts, Y-axis: 2 theta angles (copper).

53 mg of the solid dispersion according to Example 4 were exposed to 75% relative humidity at 40° C. for four weeks. Afterwards, the solid dispersion was analyzed using PXRD which confirmed that [(7R)-4-(5-chloro-1,3-benzoxazol-2-yl)-7-methyl-1,4-diazepan-1-yl][5-methyl-2-(2H-1, 2,3-triazol-2-yl)phenyl]methanone underwent no crystallization in the presence of Soluplus® after four weeks (cf. FIG. 4).

Example 7: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Methocel® E5 as Polymer (Matrix Compound)

168 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 168 mg of Methocel E5 were suspended in 50 mL $CH_2Cl_2$. The solvent of the clear solution was evaporated on a rotavapor and the residue was dried under vacuum at room temperature for 18 hours.

Figure 5:
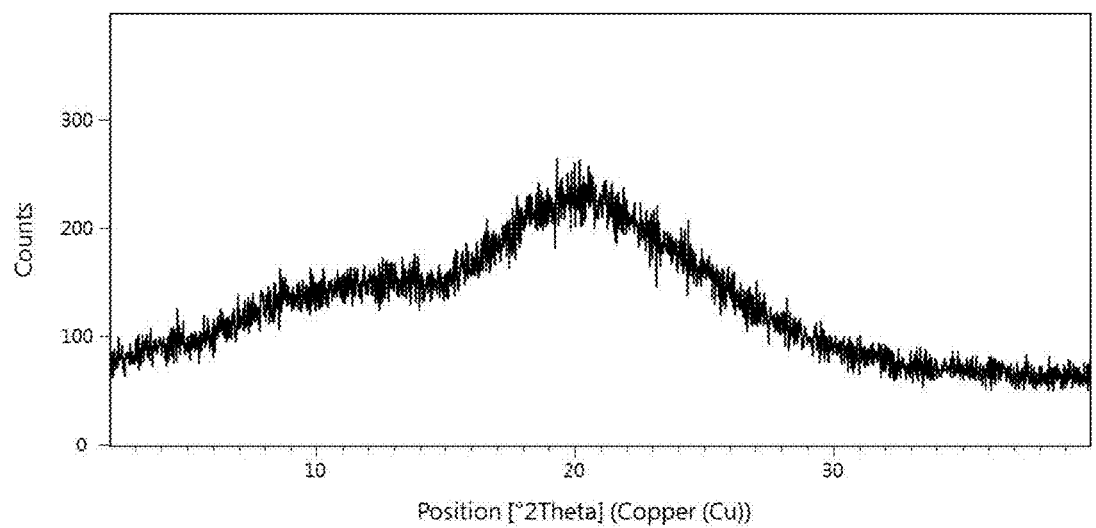
FIG. 5: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl]methanone and hydroxypropylmethylcellulose (Methocel® E5) with a weight ratio of 1:1. The Y-axis shows the counts, the X-axis precision of the 2 theta angle (copper).

The resulting solid dispersion was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 5).

Example 8: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Methocel® E5 as Polymer (Matrix Compound)

109 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 109 mg of Methocel® E5 were dissolved in a solvent mixture of 23 mL THF and 6 mL $H_2O$. Subsequently the solvent was evaporated on a rotavapor at 40° C. and the residue was dried under vacuum for 18 hours.

Example 9: Stability of the Solid Dispersion According to Example 7

Figure 6:
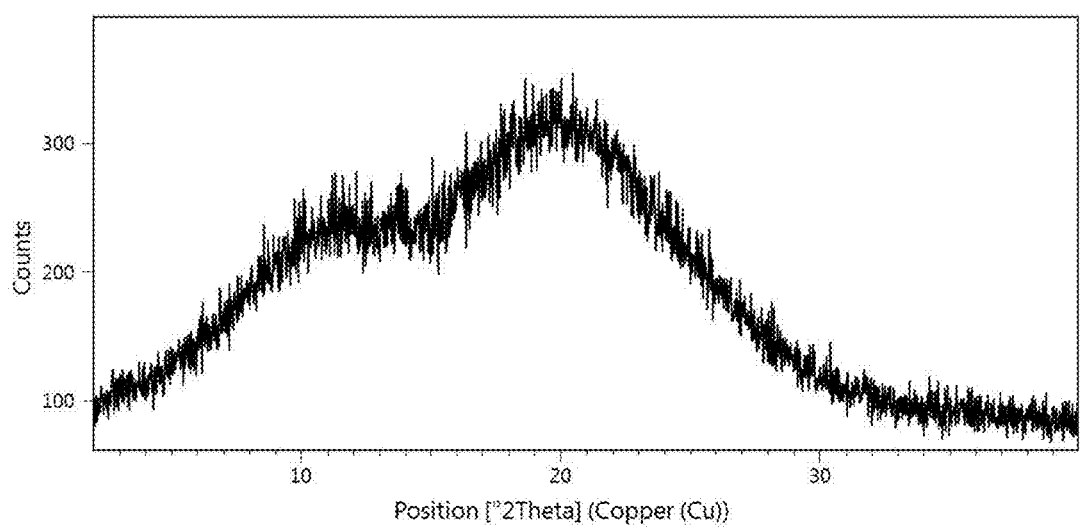
FIG. 6: shows the PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with hydroxypropylmethylcellulose (Methocel® E5) with a weight ratio 1:1 after storage for four weeks at 40° C. and a relative humidity of 75%. X-axis: counts, Y-axis: 2 theta angles (copper).

53 mg of the solid dispersion according to Example 7 were exposed to 75% relative humidity at 40° C. for four weeks. Afterwards, the solid dispersion was analyzed using PXRD which confirmed that [(7R)-4-(5-chloro-1,3-benzoxazol-2-yl)-7-methyl-1,4-diazepan-1-yl][5-methyl-2-(2H-1,2,3-triazol-2-yl)phenyl]methanone underwent no crystallization in the presence of Soluplus® after four weeks (cf. FIG. 6).

Example 10: Preparation of a Solid Dispersion of [(7R)-4-(5-chloro-1,3-benzoxazol-2-yl)-7-methyl-1,4-diazepan-1-yl][5-methyl-2-(2H-1,2,3-triazol-2-yl)phenyl]methanone with Syloid® 72 FP as Carrier (Matrix Compound)

Figure 7:
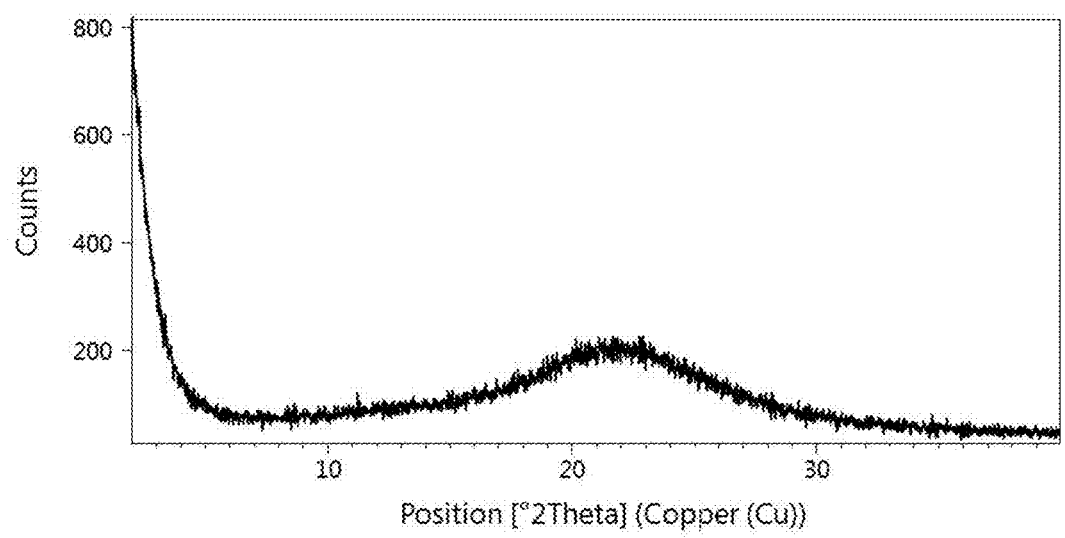
FIG. 7: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone and Syloid® 72 FP with a weight ratio of 1:1. The Y-axis shows the counts, the X-axis precision of the 2 theta angle (copper).

152 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 153 mg of Syloid® 72 FP were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl][5-methyl-2-(2H-1,2,3-triazol-2-yl)phenyl]methanone was present in amorphous form (cf. FIG. 7).

Example 11: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Syloid® 244 FP as Carrier (Matrix Compound)

Figure 8:
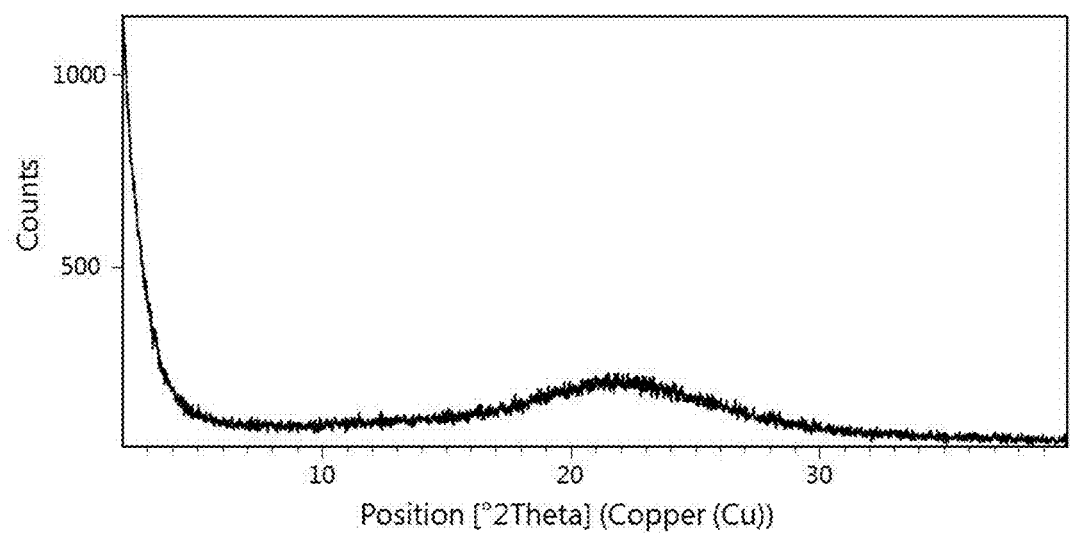
FIG. 8: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone and Syloid® 244 FP with a weight ratio of 1:1. The Y-axis shows the counts, the X-axis precision of the 2 theta angle (copper).

159 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 160 mg of Syloid® 244 FP were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 8).

Example 12: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Syloid® AL-1 FP as Carrier (Matrix Compound)

Figure 9:
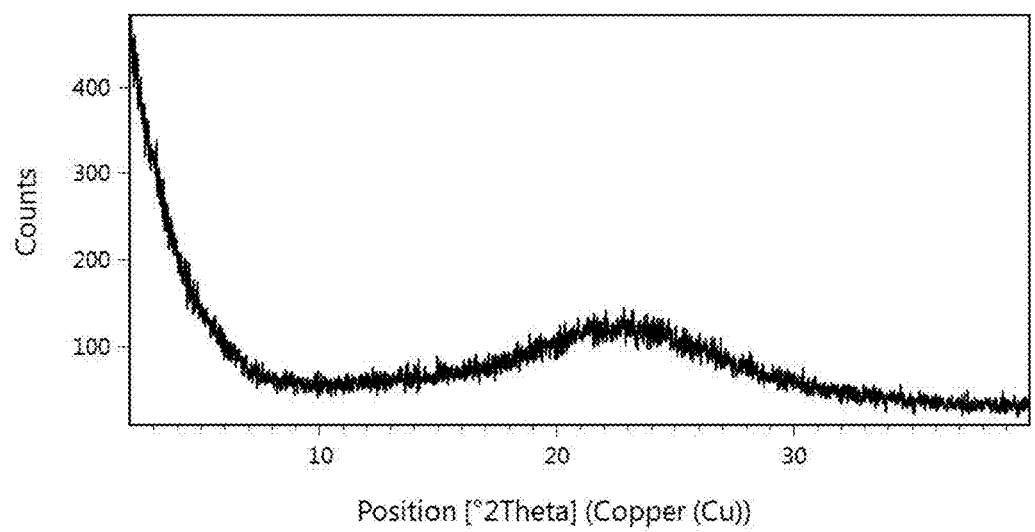
FIG. 9: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone and Syloid® AL-1 FP with a weight ratio of 1:1. The Y-axis shows the counts, the X-axis precision of the 2 theta angle (copper).

167 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 169 mg of Syloid® AL-1 FP were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 9).

Example 13: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Aerosil® 200 as Carrier (Matrix Compound)

Figure 10:
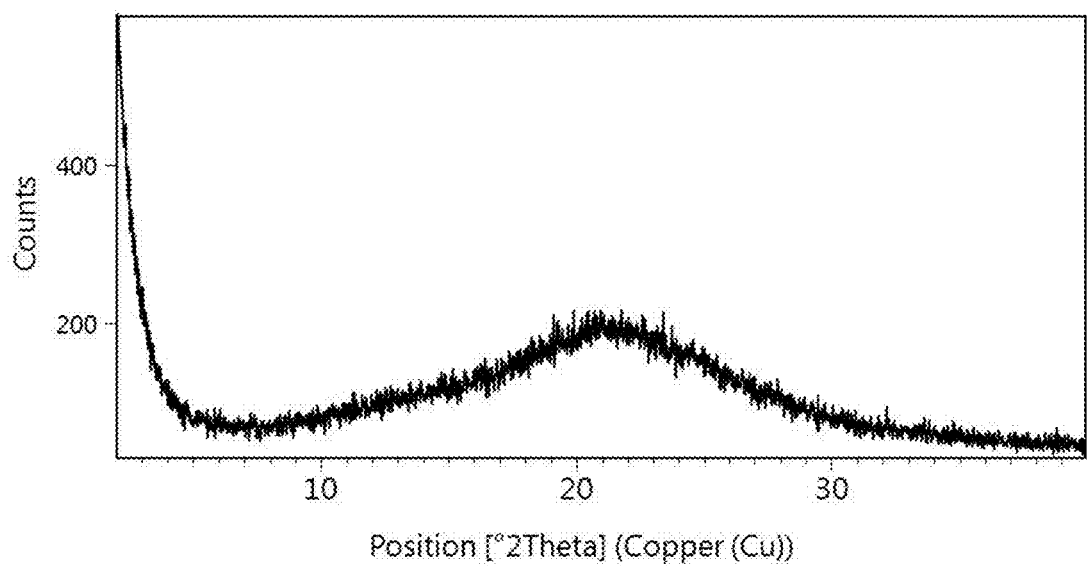
FIG. 10: shows a PXRD pattern of a solid dispersion of [(7R)-4-(5-chloro-1,3-benzoxazol-2-yl)-7-methyl-1,4-diazepan-1-yl][5-methyl-2-(2H-1,2,3-triazol-2-yl)phenyl] methanone and Aerosil® 200 with a weight ratio of 1:1. The Y-axis shows the counts, the X-axis precision of the 2 theta angle (copper).

163 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 168 mg of Aerosil® 200 were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl][5-methyl-2-(2H-1,2,3-triazol-2-yl)phenyl] methanone was present in amorphous form (cf. FIG. 10).

Example 14: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Neusilin® US2 as Carrier (Matrix Compound)

Figure 11:
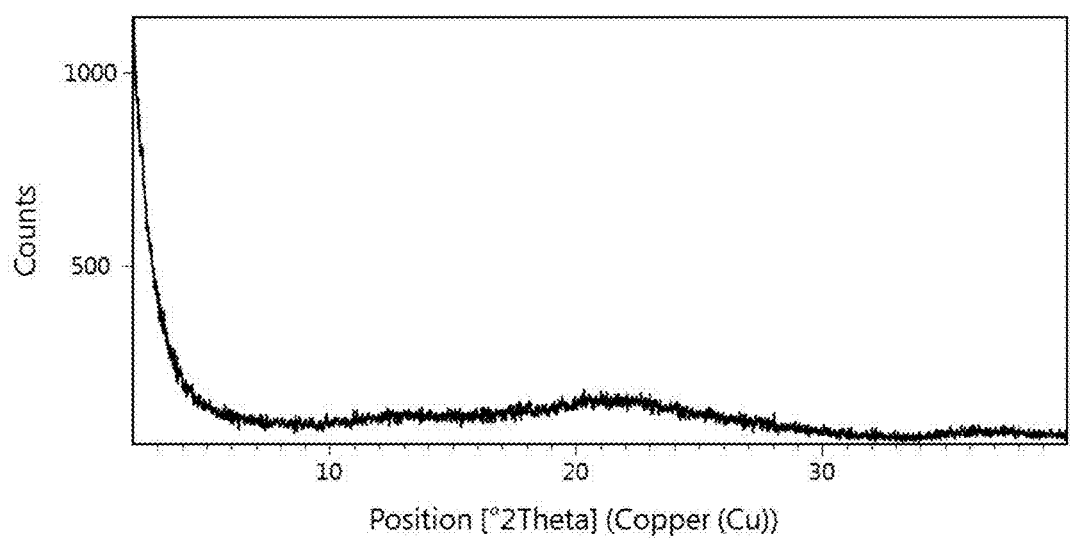
FIG. 11: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone and Neusilin® US2 with a weight ratio of 1:1. The Y-axis shows the counts, the X-axis precision of the 2 theta angle (copper).

153 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 154 mg of Neusilin® US2 were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 11).

Example 15: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Neusilin® UFL2 as Carrier (Matrix Compound)

Figure 12:
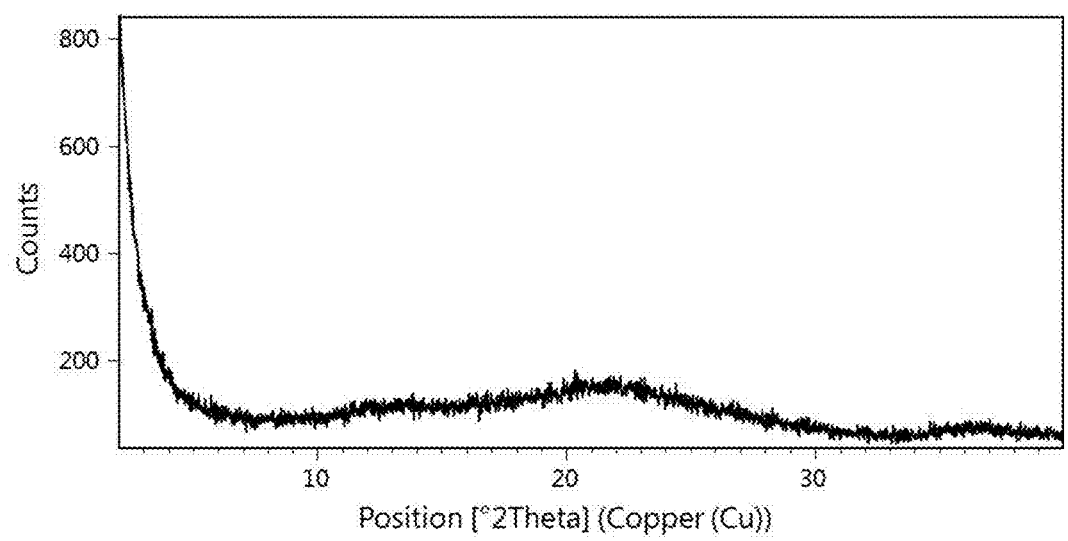
FIG. 12: shows a PXRD pattern of a solid dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone and Neusilin® UFL2 with a weight ratio of 1:1. The Y-axis shows the counts, the X-axis precision of the 2 theta angle (copper).

153 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and 155 mg of Neusilin® UFL2 were suspended in 50 mL $CH_2Cl_2$. The suspension was stirred at room temperature for 15 hours. Subsequently, the solvent was removed on a rotavapor at 40° C. The residue was dried under vacuum at room temperature for 2 days. The resulting solid dispersion was analyzed using PXRD which showed that the [(7R)-4-(5-chloro-1,3-benzoxazol-2-yl)-7-methyl-1,4-diazepan-1-yl][5-methyl-2-(2H-1,2,3-triazol-2-yl) phenyl]methanone was present in amorphous form (cf. FIG. 12).

Example 16: Preparation of Solid Dispersions by Spray Drying 750 mg suvorexant and 250 mg polymer as indicated in tables 1 and 2 below were dissolved in 250 mL dichloromethane at room temperature. Amorphous solid dispersions were obtained by spray-drying with the following parameters:

TABLE 1

| Spray-drying parameters | | |
| --- | --- | --- |
| inlet temperature [° C.] | outlet temperature [° C.] | spray rate of feed [mL/min] |
| 43-55 | 33-40 | 3-5 |

The yields are listed in the following Table 2:

TABLE 2

| Yields obtained | |
| --- | --- |
| polymer | yield [%] |
| HPMC | 89 |
| HPC | 91 |
| Soluplus | 94 |

II. Characterization of the Solid Dispersions

X-ray powder diffraction patterns were obtained with a PANalytical X'Pert PRO diffractometer equipped with a theta/theta coupled goniometer in transmission geometry, Cu-Kalpha1,2 radiation (wavelength 0.15419 nm) with a focusing mirror and a solid state PIXcel detector. The patterns were recorded at a tube voltage of 45 kV and a tube current of 40 mA, applying a stepsize of 0.013° 2-Theta with 40 s per step (255 channels) in the angular range of 2 to 40° 2-Theta at ambient conditions.

III. Preparation of Amorphous Suvorexant

III.1 Preparation by Spray-Drying

Example 17: Preparation the Amorphous Form of [(7R)-4-(5-chloro-1,3-benzoxazol-2-yl)-7-methyl-1,4-diazepan-1-yl] [5-methyl-2-(2H-1,2,3-triazol-2-yl) phenyl] methanone Via Spray Drying 1 g suvorexant was dissolved in 50 mL dichloromethane at room temperature. Amorphous suvorexant was obtained by spray-drying through the nozzle of a Büchi Spray Dryer. The process parameters were set as follows:

TABLE 3

| Spray-drying parameters | | |
| --- | --- | --- |
| inlet temperature [° C.] | outlet temperature [° C.] | spray rate of feed [mL/min] |
| 43-55 | 33-40 | 3-5 |

The amorphous suvorexant was obtained in 95% yield.

III.2 Preparation by Evaporation on a Rotavapor

Figure 13:
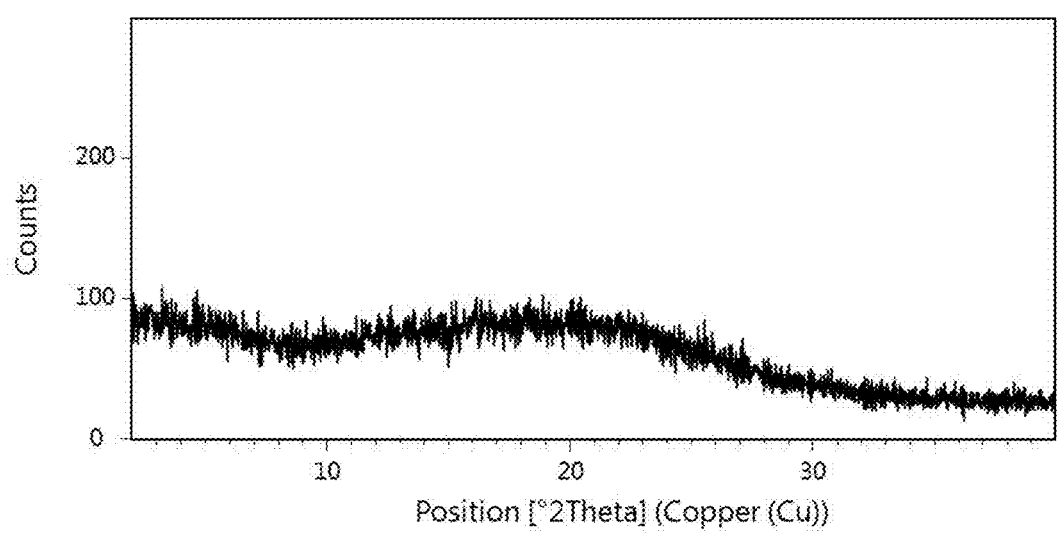
FIG. 13: shows a PXRD pattern of amorphous [(7R)-4-(5-chloro-1,3-benzoxazol-2-yl)-7-methyl-1,4-diazepan-1-yl] [5-methyl-2-(2H-1,2,3-triazol-2-yl)phenyl] methanone. The Y-axis shows the counts, the X-axis precision of the 2 theta angle (copper).
Figure 14:
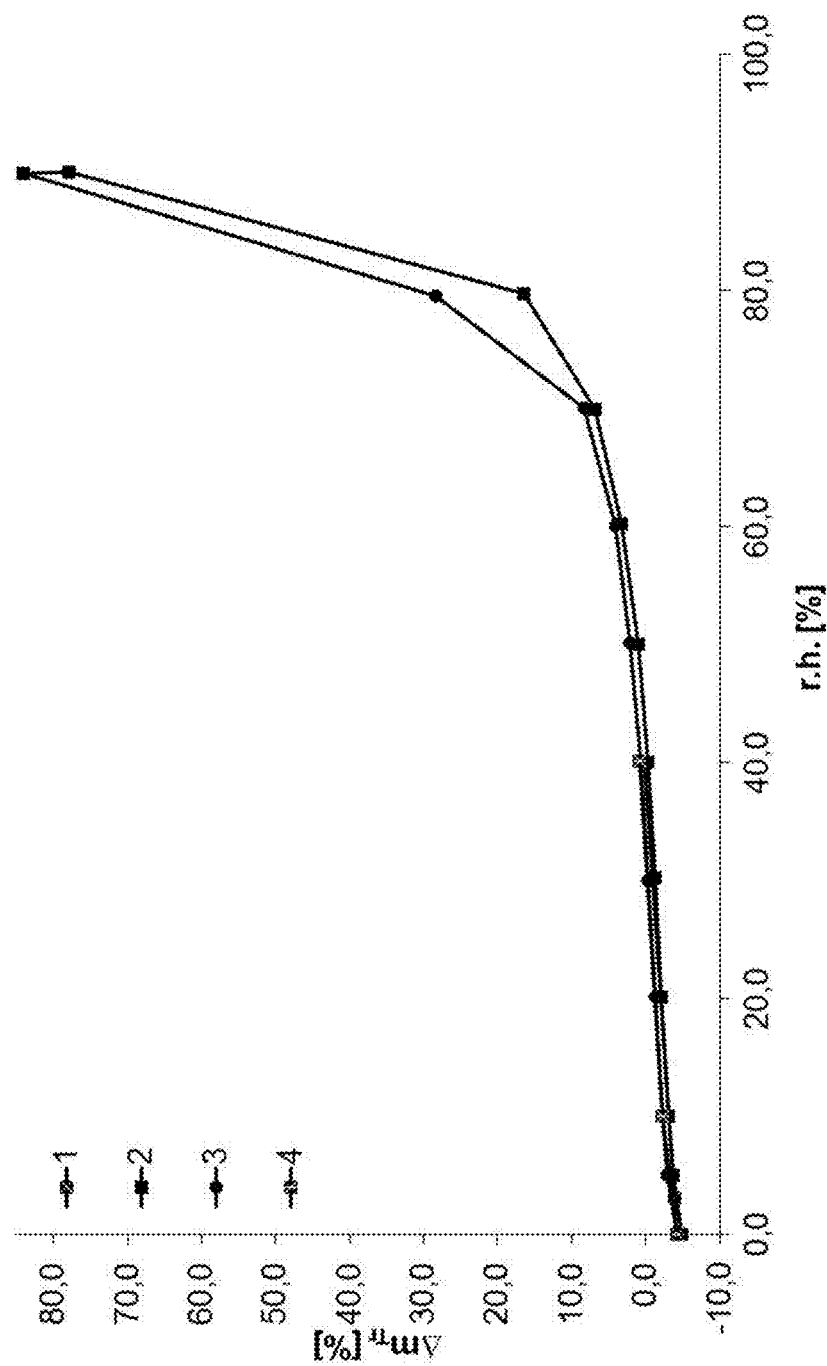
FIG. 14: shows the DVS isotherm of the matrix compound Syloid® 72 FP, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −10.0; 0.0; 10.0; 20.0; 30.0; 40.0; 50.0; 60.0; 70.0; 80.0; and 90.0. The Δm(desorption) values are obtained from the desorption isotherm (symbols: ●), the Δm(adsorption) values are obtained from the adsorption isotherm (symbols: ■).
Figure 15:
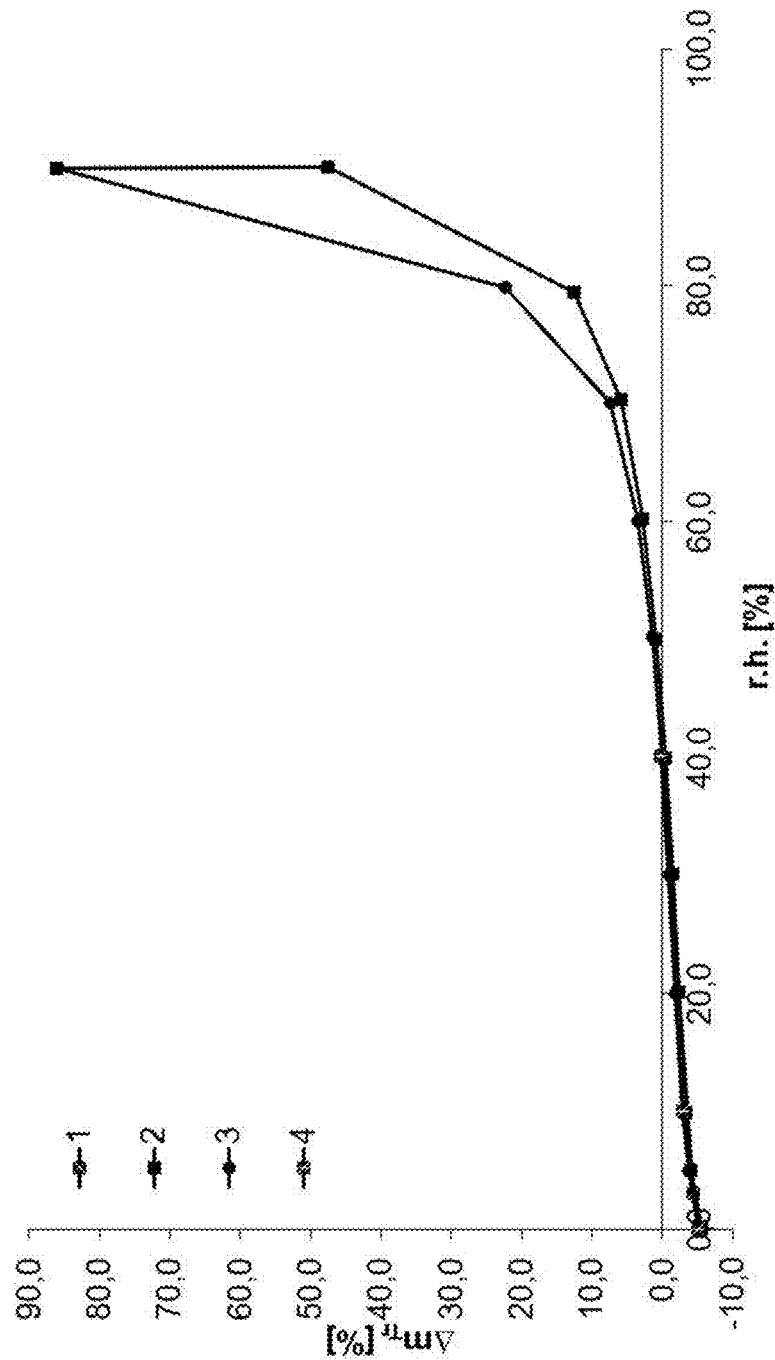
FIG. 15: shows the DVS isotherm of the matrix compound Syloid® 244 FP, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −20.0; 0.0; 20.0; 40.0; 60.0; 80.0; and 100.0. The Δm(desorption) values are obtained from the desorption isotherm (symbols: ●), the Δm(adsorption) values are obtained from the adsorption isotherm (symbols: ■).
Figure 16:
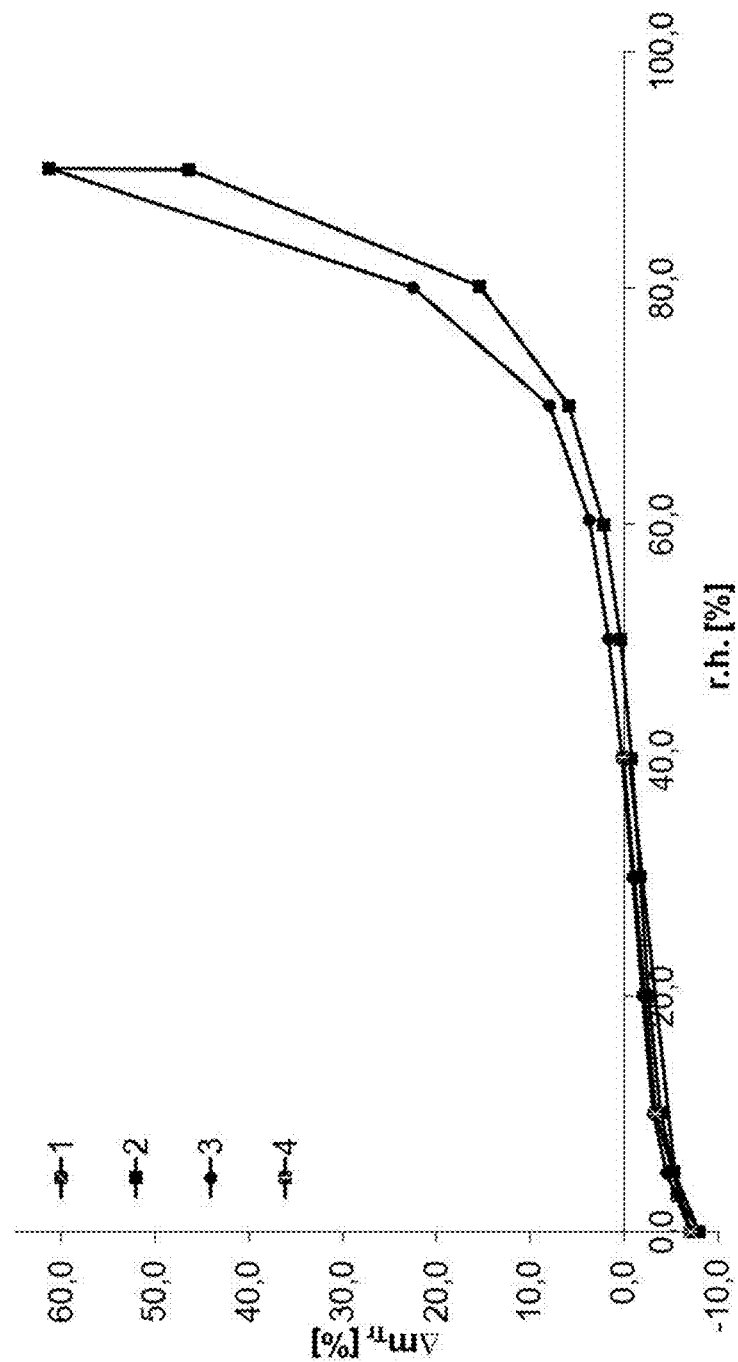
FIG. 16: shows the DVS isotherm of the matrix compound Neusilin® UFL2, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −20.0; −10.0; 0.0; 10.0; 20.0; 30.0; 40.0; 50.0; 60.0; and 70.0. The Δm(desorption) values are obtained from the desorption isotherm (symbols: ●), the Δm(adsorption) values are obtained from the adsorption isotherm (symbols: ■).
Figure 17:
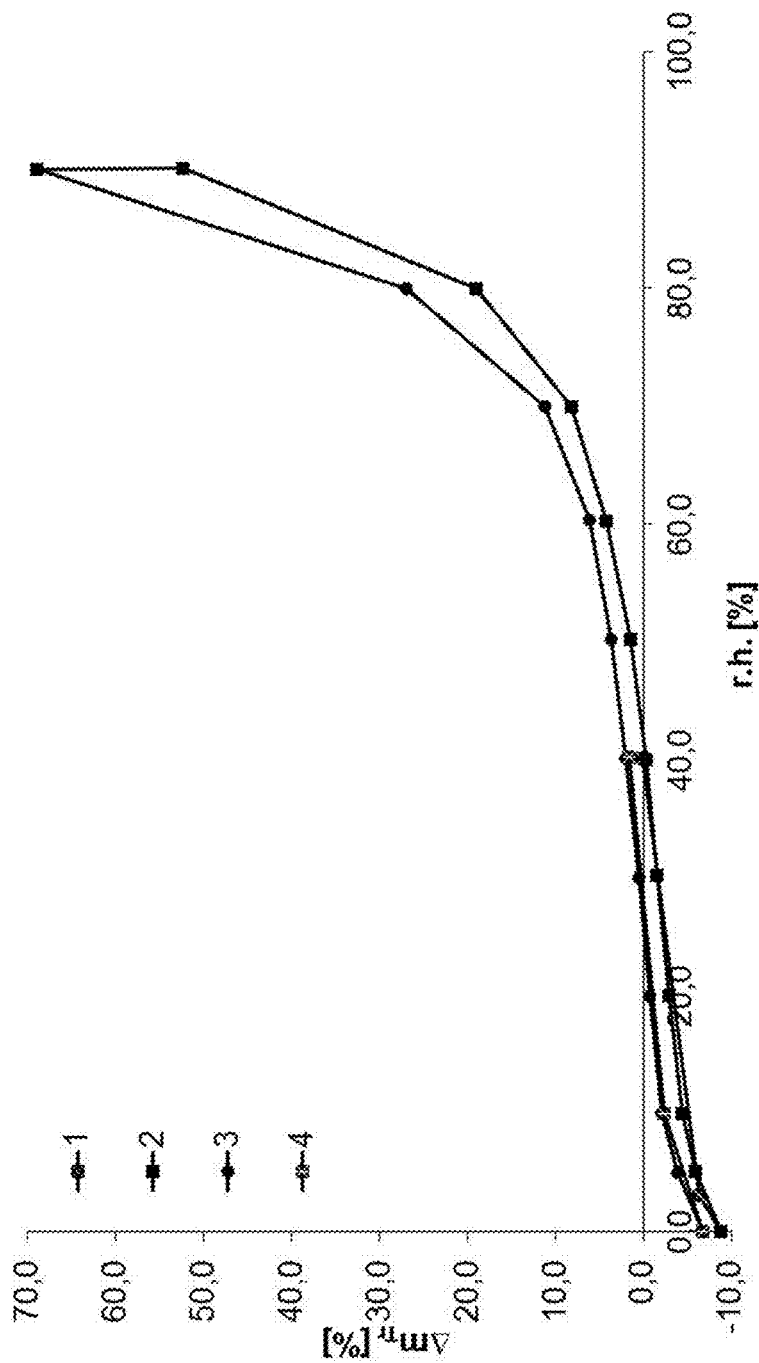
FIG. 17: shows the DVS isotherm of the matrix compound Neusilin® US2, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −20.0; −10.0; 0.0; 10.0; 20.0; 30.0; 40.0; 50.0; 60.0; 70.0; and 80.0. The Δm(desorption) values are obtained from the desorption isotherm (symbols: ●), the Δm(adsorption) values are obtained from the adsorption isotherm (symbols: ■).
Figure 18:
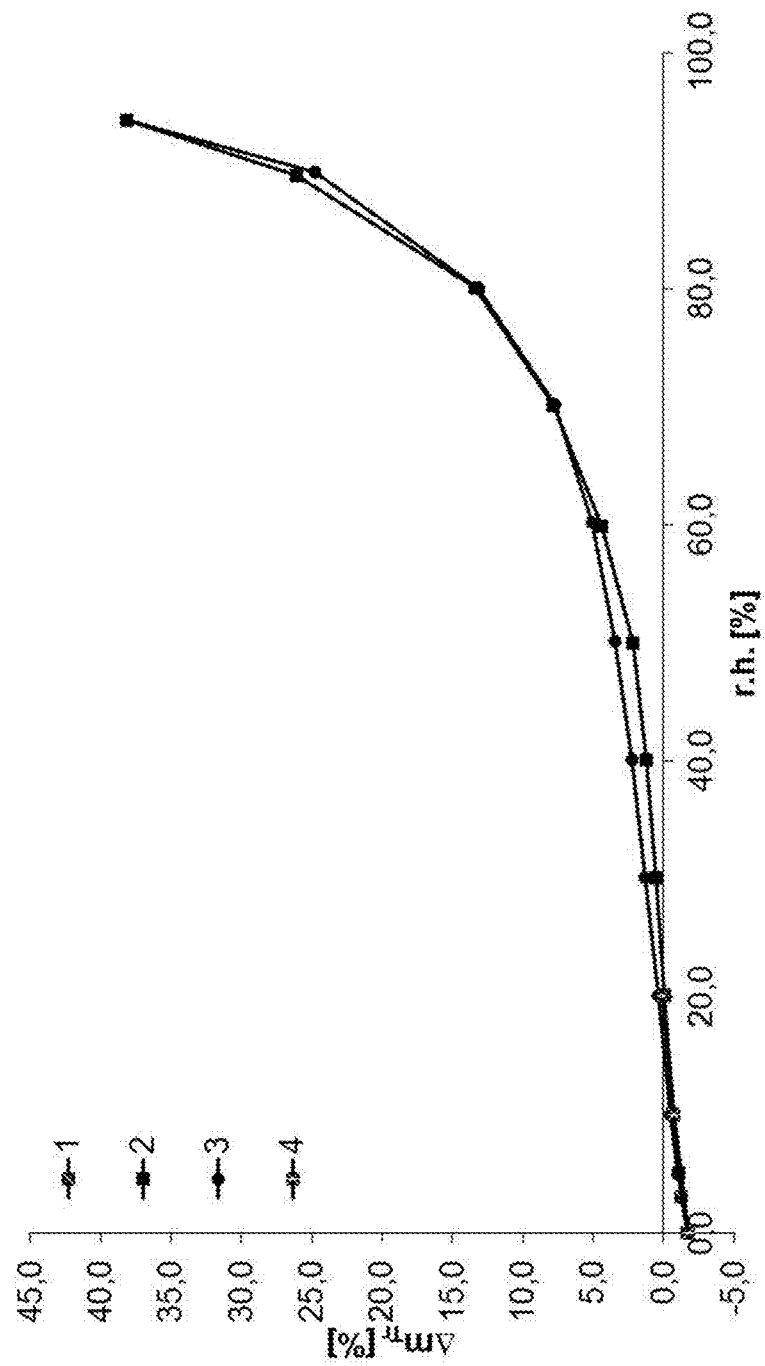
FIG. 18: shows the DVS isotherm of the matrix compound Soluplus, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −5.0; 0.0; 5.0; 10.0; 15.0; 20.0; 25.0; 30.0; 35.0; 40.0; and 45.0. The Δm(desorption) values are obtained from the desorption isotherm (symbols: ●), the Δm(adsorption) values are obtained from the adsorption isotherm (symbols: ■).
Figure 19:
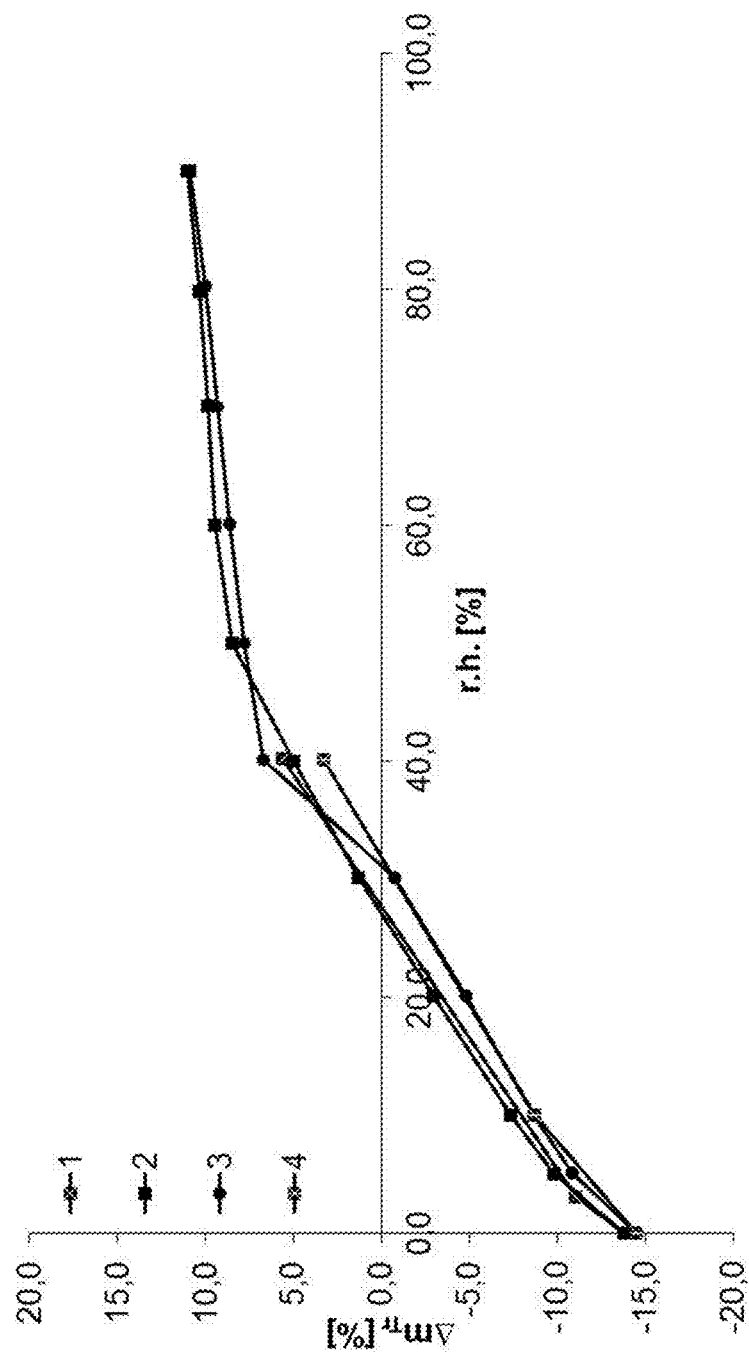
FIG. 19: shows the DVS isotherm of the matrix compound Syloid® AL-1 FP, recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −20.0; −15.0; −10.0; −5.0; 0.0; 5.0; 10.0; and 15.0. The Δm(desorption) values are obtained from the desorption isotherm (symbols: ●), the Δm(adsorption) values are obtained from the adsorption isotherm (symbols: ■).
Figure 20:
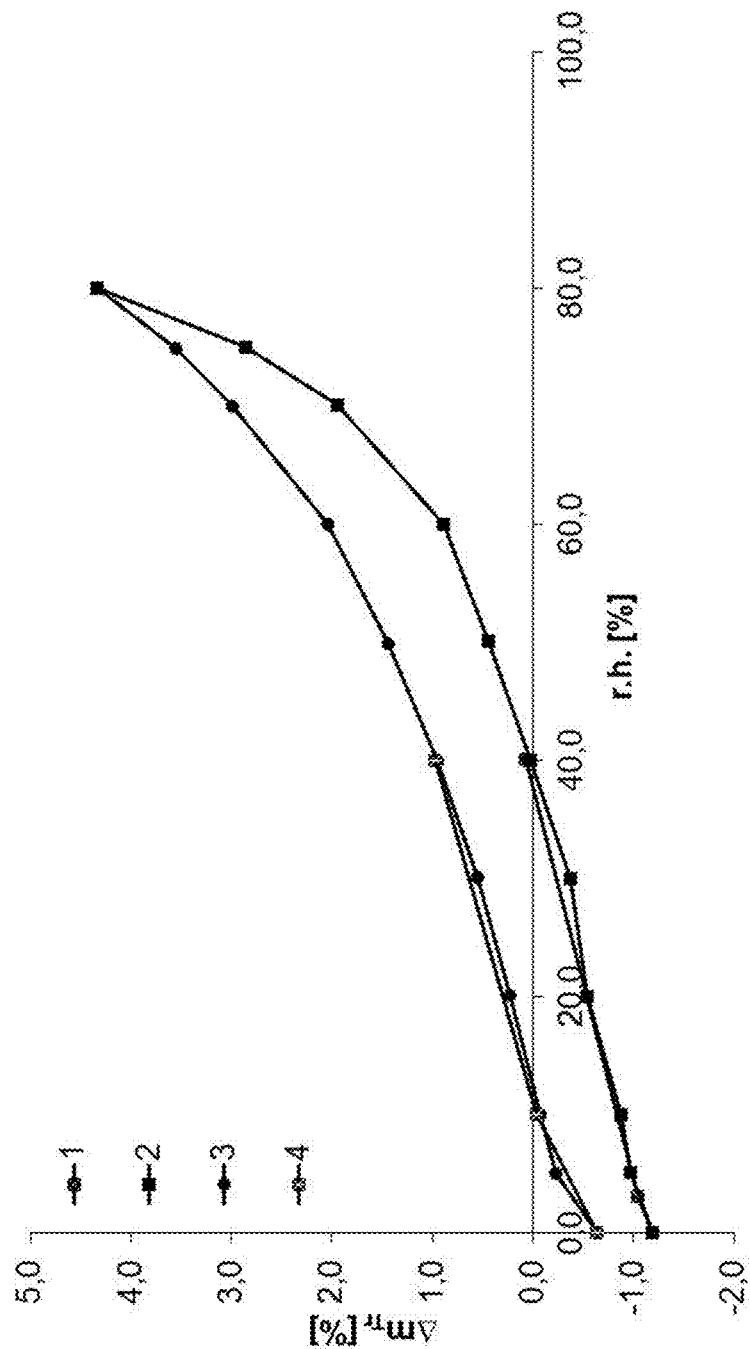
FIG. 20: shows the DVS isotherm of the matrix compound Aerosil® 200 recorded as described in Example V. The x axis shows the r.h. (relative humidity, in %) values, with tick marks, from left to right, at 0.0; 10.0; 20.0; 30.0; 40.0; 50.0; 60.0; 70.0; 80.0; 90.0; and 100.0. The y axis shows the Δm values (in %), with tick marks, from bottom to top, at −2.0; −1.0; 0.0; 1.0; 2.0; 3.0; 4.0; and 5.0. The Δm(desorption) values are obtained from the desorption isotherm (symbols: ●), the Δm(adsorption) values are obtained from the adsorption isotherm (symbols: ■).
Figure 21:
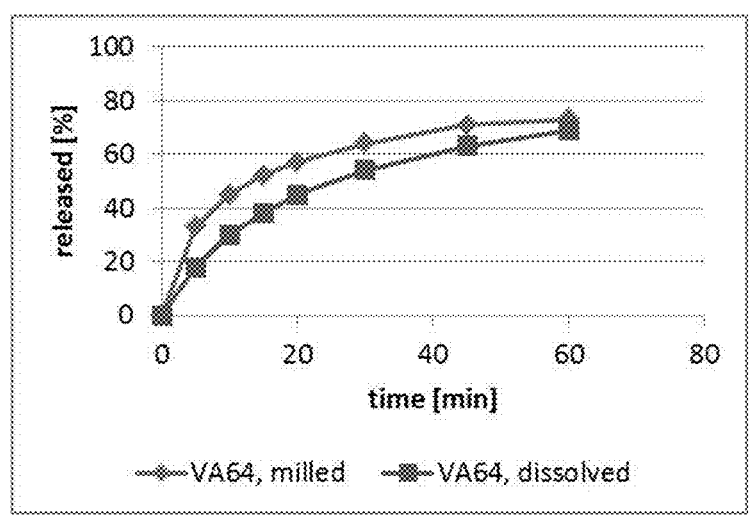
FIG. 21: shows the dissolution profiles of the tablets according to Example VII.21 prepared based solid dispersions comprising Kollidon® VA64. The x axis shows the time/min with tick marks, from left to right, at 0, 20, 40, 60, 80. The y axis shows the amount of suvorexant released/%, based on the suvorexant content of the tablet prior to dissolution, with tick marks, from bottom to top, at 0, 20, 40, 60, 80, 100. The symbol ♦ indicates the values for the tablets obtained from solid dispersion prepared by dissolving and drying, the symbol ■ indicates the values for the tablets obtained from solid dispersion prepared by milling.
Figure 22:
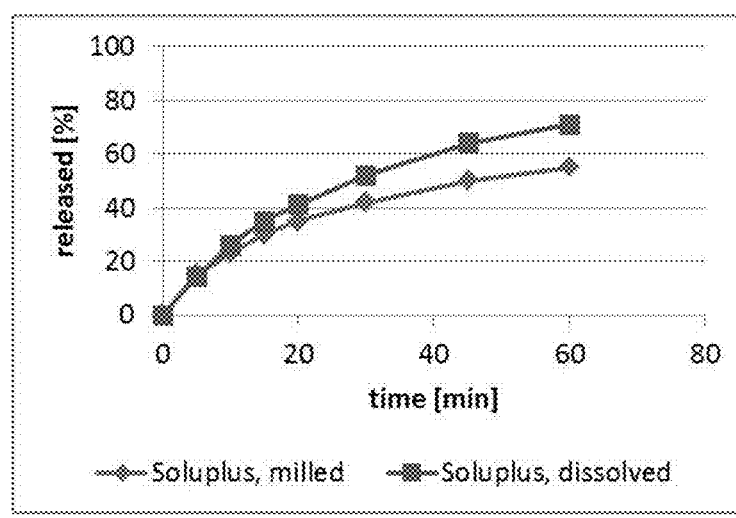
FIG. 22: shows the dissolution profiles of the tablets according to Example VII.21 prepared based solid dispersions comprising Soluplus®. The x axis shows the time/min with tick marks, from left to right, at 0, 20, 40, 60, 80. The y axis shows the amount of suvorexant released/%, based on the suvorexant content of the tablet prior to dissolution, with tick marks, from bottom to top, at 0, 20, 40, 60, 80, 100. The symbol ♦ indicates the values for the tablets obtained from solid dispersion prepared by dissolving and drying, the symbol ■ indicates the values for the tablets obtained from solid dispersion prepared by milling.
Figure 23:
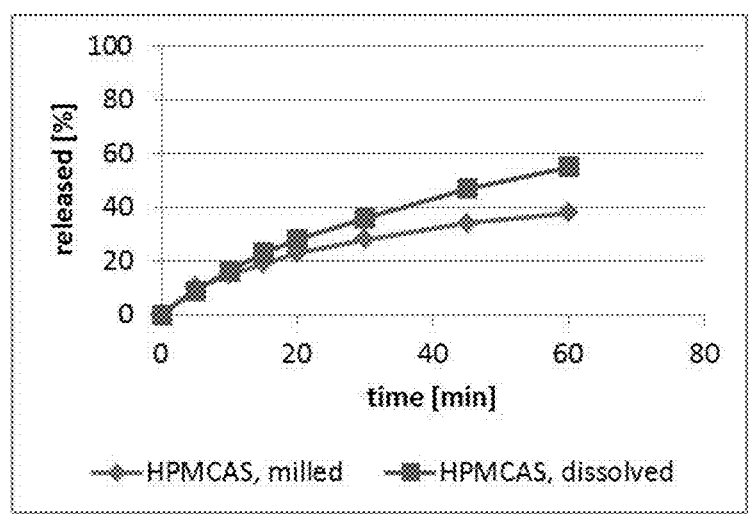
FIG. 23: shows the dissolution profiles of the tablets according to Example VII.21 prepared based solid dispersions comprising HPMCAS. The x axis shows the time/min with tick marks, from left to right, at 0, 20, 40, 60, 80. The y axis shows the amount of suvorexant released/%, based on the suvorexant content of the tablet prior to dissolution, with tick marks, from bottom to top, at 0, 20, 40, 60, 80, 100. The symbol ♦ indicates the values for the tablets obtained from solid dispersion prepared by dissolving and drying, the symbol ■ indicates the values for the tablets obtained from solid dispersion prepared by milling.
Figure 24:
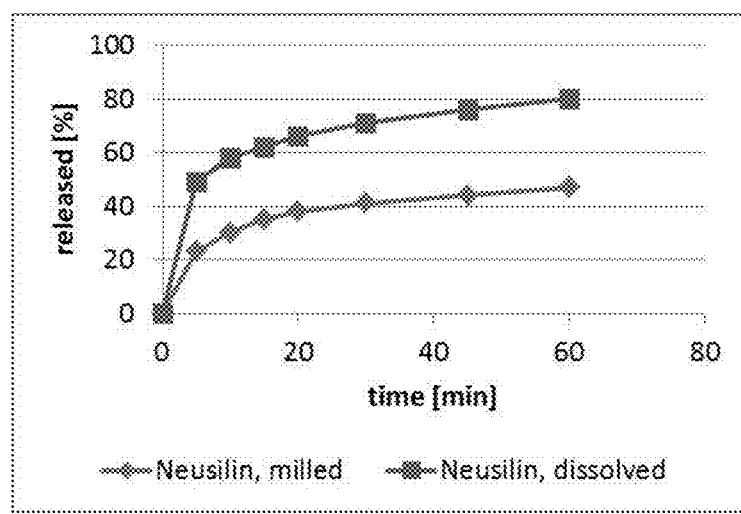
FIG. 24: shows the dissolution profiles of the tablets according to Example VII.21 prepared based solid dispersions comprising Neusilin® UFL. The x axis shows the time/min with tick marks, from left to right, at 0, 20, 40, 60, 80. The y axis shows the amount of suvorexant released/%, based on the suvorexant content of the tablet prior to dissolution, with tick marks, from bottom to top, at 0, 20, 40, 60, 80, 100. The symbol ♦ indicates the values for the tablets obtained from solid dispersion prepared by dissolving and drying, the symbol ■ indicates the values for the tablets obtained from solid dispersion prepared by milling.

Example 18: Preparation the Amorphous Form of [(7R)-4-(5-chloro-1,3-benzoxazol-2-yl)-7-methyl-1,4-diazepan-1-yl] [5-methyl-2-(2H-1,2,3-triazol-2-yl) phenyl] methanone 200 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone were dissolved in 5 mL $CH_2Cl_2$. The solvent was evaporated on a rotavapor at 40° C., the residue was dried under vacuum at room temperature for 2 days. The resulting solid was analyzed using PXRD which showed that the [(7R)-4-(5-chloro-1,3-benzoxazol-2-yl)-7-methyl-1,4-diazepan-1-yl] [5-methyl-2-(2H-1,2,3-triazol-2-yl)phenyl] methanone was present in amorphous form (cf. FIG. 13).

III.3 Characterization

See above under paragraph II.

IV. Determination of the Moisture Stability 20-200 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone and a specific amount of the matrix compound relative to the amount of the API as indicated in Table 3 below were suspended in 50 mL $CH_2Cl_2$. The suspension was stirred at room temperature for 15 hours. Subsequently, the solvent was removed on a rotavapor at 40° C. The residue was dried under vacuum at room temperature for 2 days to give a solid dispersion comprising suvorexant in amorphous only. The long term stability was measured as follows: 40-100 mg of a given solid composition were exposed to an atmosphere having a relative humidity of 75% and a temperature of 40° C. for a period of time as indicated in Table 3 below, if stable and if not having deliquesced, and analysed via XRD as described above in paragraph II with respect to the amorphousness.

TABLE 4

| matrix compound | API loading [weight-%, based on the total weight of the sum of API + matrix compound] | t (time of stability) |
|---|---|---|
| none | 100 | 1 week < t < 2 weeks |
| Soluplus ® | 20 | 1 day < t < 1 week |
|  | 40 | 1 day < t < 1 week |
|  | 50 | t > 4 weeks |
|  | 60 | t > 4 weeks |
|  | 80 | t > 4 weeks |
|  | 95 | t > 4 weeks |
| HPMCAS | 50 | t > 4 weeks |
|  | 60 | t > 4 weeks |
|  | 80 | t > 4 weeks |
|  | 95 | t > 4 weeks |
| Methocel ® E5 | 50 | t > 4 weeks |
|  | 60 | t > 4 weeks |
|  | 80 | t > 4 weeks |
|  | 95 | t > 4 weeks |
| Syloid ® 72 FP | 20 | t > 4 weeks |
|  | 40 | t > 4 weeks |
|  | 50 | t > 6 weeks |
|  | 60 | 1 week < t < 2 weeks |
|  | 75 | <1 day |
| Syloid ® 244 FP | 20 | t > 4 weeks |
|  | 40 | t > 4 weeks |
|  | 50 | t > 6 weeks |
|  | 60 | t > 4 weeks |
|  | 75 | <1 day |
| Syloid ® AL-1 FP | 20 | t > 4 weeks |
|  | 40 | 1 day < t < 10 days |
|  | 50 | 1 day < t < 2 weeks |
| Neusilin ® US2 | 20 | t >4 weeks |
|  | 40 | t >4 weeks |
|  | 50 | t >6 weeks |
|  | 60 | 1 day < t < 1 week |
|  | 75 | 1 day < t < 1 week |
|  | 95 | 1 day < t < 1 week |
| Neusilin ® UFL | 20 | t > 4 weeks |
|  | 40 | t > 4 weeks |
|  | 50 | t > 2 weeks |
|  | 60 | 2 weeks < t < 4 weeks |
| Aerosil ® 200 | 20 | t > 4 weeks |
|  | 40 | t > 4 weeks |
|  | 50 | t > 4 weeks |
|  | 60 | t > 4 weeks |

V. Dynamic Vapor Sorption (DVS) Measurements at 75% Relative Humidity and 25° C.

The adsorption-desorption isotherms from which the values of Δm(desorption) and Δm(adsorption) at 75% relative humidity and at 25° C. were obtained, were recorded with an SPSx-1μ moisture sorption analyzer (ProUmid GmbH & Co. KG, Ulm, Germany). The measurement cycle was started at 40% relative humidity (RH) and first decreased to 3% RH and 0% RH. Then RH was increased to 5% to 10% RH, afterwards to 90% RH in 10% steps and further to 95% RH. The desorption cycle started with a 5% step to 90% RH, then from 90% to 10% RH in 10% steps, to 5% RH and to 0% RH. The last step was the increase of RH to 40%. The time per step was set to a minimum of 1 hour and a maximum of 3 hours. If an equilibrium condition with a constant mass of ±0.01% within 1 hour was reached before the maximum time for all examined samples the sequential humidity step was applied before the maximum time of 3 hours. If no equilibrium was achieved the consecutive humidity step was applied after the maximum time of 3 hours. The temperature was (25±0.1)° C.

To obtain the Δm(desorption) and Δm(adsorption) values, the recorded adsorption-desorption isotherms shown in the Figures of the present invention were analysed by comparing the value of Δm(desorption), plotted on the y axis, of a given desorption isotherm with the value of Δm(adsorption), plotted on the y axis, of the respective adsorption isotherm, both at 75% r.h., plotted on the x axis.

VI. Preparation of Solid Dispersions

Example 19: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Kollidon® VA64 as Carrier (Matrix Compound) and Kolliphor® P188 Micro as Surfactant 781 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone, 360 mg Kollidon VA64 and 60 mg Kolliphor P188 micro were dissolved in 10 mL dichloromethane. After filtration, the clear solution was evaporated on a rotavapor at 40° C. The foam-like residue was dried under vacuum at room temperature for 18 hours.

Example 20: Preparation of a Solid Dispersion of [(7R)-4-(5-chloro-1,3-benzoxazol-2-yl)-7-methyl-1,4-diazepan-1-yl] [5-methyl-2-(2H-1,2,3-triazol-2-yl)phenyl] methanone with Kollidon® VA64 as Carrier (Matrix Compound) and Tween® 80 as Surfactant 783 mg of [(7R)-4-(5-chloro-1,3-benzoxazol-2-yl)-7-methyl-1,4-diazepan-1-yl][5-methyl-2-(2H-1,2,3-triazol-2-yl)phenyl]methanone, 361 mg Kollidon VA64 were dissolved in 10 mL dichloromethane. 60 mg Tween 80 were dissolved in 5 mL dichloromethane. The two solutions were combined and filtrated. Then the clear solution was evaporated on a rotavapor at 40° C. The foam-like residue was dried under vacuum at room temperature for 18 hours.

VII. Preparation of Tablets

Example 21: Preparation of Compositions Comprising a Solid Dispersion of Suvorexant in the Form of Tablets Tablets were prepared employing the solid dispersions comprising amorphous suvorexant. The solid dispersions were prepared either by dissolving (steps (a), (b), and (c), as described herein), or by milling (steps (a'), (b') and (c'), as described herein). In particular, with regard to the preparation of the solid dispersions by dry-milling the components as indicated, using a Retsch mill having a 25 ml milling cell, wherein milling was carried out for 20 min at a milling frequency of 27.5 Hz. The tablets prepared had the following composition as described in Table 5. As matrix compounds, Kollidon® VA64, Soluplus®, HPMCAS and Neusilin® UFL were used.

TABLE 5

| General composition of tablets | |
|---|---|
| Component of tablet | Amount component/mg |
| Amorphous Suvorexant | 20.00* |
| Matrix compound | 10.80* |
| Microcrystalline cellulose (Avicel ® PH 15) | 82.50 |
| Lactose monohydrate (FlowLac ® 100) | 110.45 |

TABLE 5-continued

General composition of tablets

| Component of tablet | Amount component/mg |
|---|---|
| Croscarmellose sodium (Ac-Di-Sol ®) | 23.00 |
| Magnesium stearate | 1.25 |
| Total weight: | 250.00 |

*Part of solid dispersion. Suvorexant concentration of solid dispersion: 65 weight-%

The tablets were prepared according to the following procedure: The solid dispersion, the microcrystalline cellulose, the lactose monohydrate and the croscarmellose sodium were mixed in a suitable container for 3-5 minutes. Magnesium stearate was added and mixed for another 1 minute. The final blend was compressed using a tooling 9 mm round into tablets. The respectively obtained tablets were subjected to a dissolution test. Thus dissolution test was carried using a paddle apparatus having a volume of 1000 ml, a rotation speed of 50 r.p.m., wherein, as dissolution medium, 0.1 M HCl was employed. The obtained dissolution profiles are shown in FIG. 21 to 24.

In Table 6 below, the results of the experiments are described. With regard to the solid dispersion employed, it is described if the suvorexant contained in the solid dispersion is amorphous after the preparation of the solid dispersion. Further, it is described if the suvorexant is stable in its amorphous form after the stability test (3 weeks at 40° C. and 75% r.h.; see section IV above). Further, it is described which dissolution values were obtained for the individual tablets.

TABLE 6

Characterization of suvorexant and tablets

| | Matrix compound | | | |
|---|---|---|---|---|
| | Kollidon | Soluplus | HPMCAS | Neusilin |
| Content of solid dispersion of matrix compound prepared by dissolving/drying/weight-% | 80 | 80 | 80 | 40 |
| Content of solid dispersion of matrix compound prepared by milling/weight-% | 65 | 65 | 65 | 65 |
| Suvorexant present in amorphous form only in solid dispersion (after dissolving/drying)? | yes | yes | yes | yes |
| Suvorexant present in amorphous form only in solid dispersion (after milling)? | yes | yes | yes | yes |
| Suvorexant present in amorphous form only in the tablets based on solid dispersion (dissolving/drying) | yes | yes | yes | yes |
| Stability test passed for tablets based on solid dispersion prepared by dissolving/drying and stored for the 3 weeks in aluminium blister? | yes | yes | yes | yes |
| Stability test passed for tablets based on solid dispersion prepared by dissolving/drying and stored for the 3 weeks in PVC blister? | yes | yes | yes | yes |
| Dissolution (after 1 hour) of tablets based on solid dispersion prepared by dissolving/drying/% | 54 | 52 | 36 | 71 |
| Dissolution (1 hour) of tablets based on solid dispersion prepared by milling/% | 64 | 42 | 28 | 41 |

Example 22: Preparation of Compositions Comprising a Solid Dispersion of Suvorexant in the Form of Tablets Further Comprising a Surfactant Tablets were prepared employing the solid dispersions comprising amorphous suvorexant.

The solid dispersions were prepared by dissolving (steps (a), (b), and (c) as described herein. As matrix compound, Kollidon® VA64 was used. In addition to the amorphous suvorexant and the matrix compound, a surfactant was employed. For the different tablets, Tween® 80, Kolliphor® 188, and SDS (sodium dodecyl sulfate) were employed. The solid dispersion had an amorphous suvorexant content of 65 weight-%, a matrix compound content of 30 weight-%, and a surfactant content of 5 weight-%.

In Table 7 below, the results of the experiments are described. With regard to the solid dispersion employed, it is described if the suvorexant contained in the solid dispersion is amorphous after the preparation of the solid dispersion.

TABLE 7

Experimental results of Example 22

| Type of surfactant | Suvorexant present in amorphous form only in solid dispersion? |
|---|---|
| None | yes |
| Tween ® 80 | yes |
| Kolliphor ® 188 | yes |
| SDS | yes |

Figure 25:
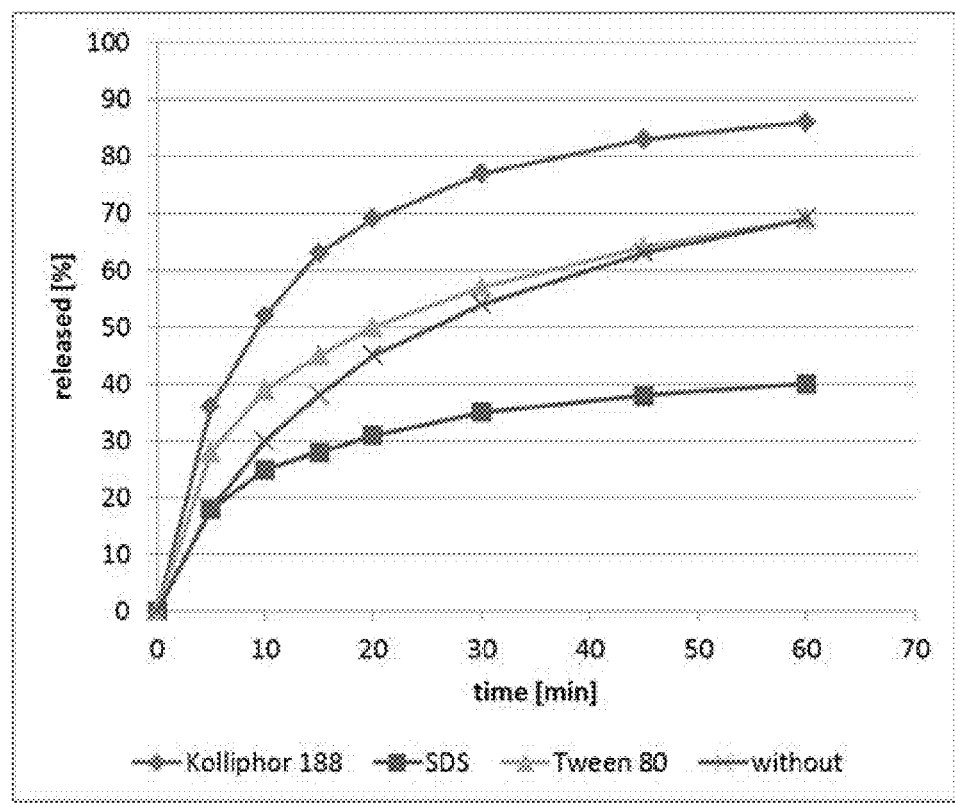
FIG. 25: shows the dissolution profiles of the tablets according to Example VII.22 prepared based solid dispersions comprising Kollidon® VA64, and additionally comprising either no surfactant (symbol: x), or Tween® 80 (symbol: ▲), or Kolliphor® 188 (symbol: ♦), or SDS (symbol: ■) as surfactant. The x axis shows the time/min with tick marks, from left to right, at 0, 10, 20, 30, 40, 50, 60, 70. The y axis shows the amount of suvorexant released/%, based on the suvorexant content of the tablet prior to dissolution, with tick marks, from bottom to top, at 0, 10, 20, 30, 40, 50, 60, 70, 80, 90, 100.

The respectively obtained tablets were subjected to a dissolution test. Thus dissolution test was carried out as described in Example 21 above. The obtained dissolution profiles are shown in FIG. 25. Clearly, Kolliphor® 188 was found to be a preferred surfactant since compared to a tablet which does not contain Kolliphor® 188, the dissolution was increased after 1 hour.

CITED LITERATURE

US 20080132490 A1
WO 2008/069997
Cox et al. (2010) *Journal of Medicinal Chemistry*, 53 (14): 5320-5332
WO 2012/148553
WO 2013/181174

The invention claimed is:

1. A solid dispersion comprising suvorexant ([(7R)-4-(5-chloro-1,3-benzoxazol-2-yl)-7-methyl-1,4-diazepan-1-yl] [5-methyl-2-(2H-1,2,3-triazol-2-yl)phenyl]methanone) or a salt thereof in amorphous form and at least one pharmaceutically acceptable matrix compound,
    wherein the at least one matrix compound is
    (i) a polymer and wherein the solid dispersion contains the suvorexant or salt thereof in an amount of at least 50 weight-% based on the combined weight of the suvorexant or salt thereof and the at least one matrix compound, or
    (ii) a silicon-based inorganic adsorbent.

2. The solid dispersion of claim 1, wherein at least 80% by weight of the suvorexant or salt thereof present in the solid dispersion is present in amorphous form.

3. The solid dispersion of claim 1, wherein in the adsorption-desorption isotherm of the at least one matrix compound in (ii), the relative mass difference Δm(adsorption) between 50% and 90% relative humidity at 25° C. is greater than or equal to 40%, determined according to dynamic vapor sorption measurement.

4. The solid dispersion of claim 1, wherein in the adsorption-desorption isotherm of the at least one matrix compound in (ii), the relative mass difference Δm(adsorption) between 0 and less than 50% relative humidity at 25° C. is less than or equal to 20%, determined according to dynamic vapor sorption measurement.

5. The solid dispersion of claim 1, wherein the polymer in (i) is a cellulose derivative or a polyvinyl caprolactam polyvinyl acetate polyethylene glycol graft polymer.

6. The solid dispersion of claim 1, wherein in the adsorption-desorption isotherm of the at least one matrix compound in (ii), the mass difference Δm(desorption) at 75% relative humidity and 25° C. is greater than or equal to the mass difference Δm(adsorption) at 75% relative humidity and 25° C., determined according to dynamic vapor sorption measurement.

7. The solid dispersion of claim 1, wherein the silicon-based inorganic adsorbent is selected from the group consisting of silica, silicates, and a combination of two or more thereof.

8. The solid dispersion of claim 1, wherein the solid dispersion in (ii) contains the suvorexant or the at least one salt thereof in an amount in the range of from 10 to 70 weight-%, based on the combined weight of the suvorexant or the at least one salt thereof and the at least one matrix compound.

9. The solid dispersion of claim 1, consisting of suvorexant or a salt thereof, the at least one matrix compound and optionally at least one solvent.

10. A process for preparing a solid dispersion comprising suvorexant or a salt thereof in amorphous form and at least one pharmaceutically acceptable matrix compound, the process comprising
    (a) providing suvorexant or a salt thereof
    (b) dissolving or dispersing suvorexant provided in (a) and the at least one matrix compound in a solvent to form a mixture
    (c) removing at least part-of the solvent
    to give the solid dispersion, and wherein the matrix compound is
    (i) a polymer and wherein the solid dispersion contains the suvorexant or salt thereof in an amount of at least 50 weight-% based on the combined weight of the suvorexant or salt thereof and the at least one matrix compound, or a silicon-based inorganic adsorbent.

11. The process of claim 10, wherein at least 80% by weight of all suvorexant comprised in the solid dispersion is amorphous.

12. The process of claim 10, wherein in step (c), the solution is evaporated.

13. A solid dispersion, obtainable or obtained by the process according to claim 10.

14. A process for the preparation of suvorexant of which at least 95 weight-%-are present in its amorphous form, comprising
    (a1) providing suvorexant of which at least 95 weight-% are present in at least one crystalline form;
    (a2) dissolving at least a portion of the suvorexant provided according to (a1) in at least one solvent, obtaining a solution comprising the suvorexant;
    (a3) subjecting at least a portion of the solution obtained according to (a2), optionally after concentrating, to rapid-drying, obtaining the suvorexant of which at least 95 weight-% are present in its amorphous form.

15. The process of claim 14, wherein the rapid drying of step (a3) is carried out by spray-drying.

16. A pharmaceutical composition, comprising a solid dispersion according to claim 1.

17. A method for treating a sleep disorder in a patient in need thereof, the method comprising administering a pharmaceutical composition, comprising a solid dispersion according to claim 1, to a patient suffering from a sleep disorder.

* * * * *